(12) United States Patent
Hendricksen et al.

(10) Patent No.: US 7,771,472 B2
(45) Date of Patent: Aug. 10, 2010

(54) BRONCHIAL FLOW CONTROL DEVICES AND METHODS OF USE

(75) Inventors: Michael J. Hendricksen, Redwood City, CA (US); Michael Barrett, Campbell, CA (US)

(73) Assignee: Pulmonx Corporation, Redwood City, CA (US)

( * ) Notice: Subject to any disclaimer, the term of this patent is extended or adjusted under 35 U.S.C. 154(b) by 1098 days.

(21) Appl. No.: 11/282,940

(22) Filed: Nov. 18, 2005

(65) Prior Publication Data

US 2006/0107956 A1     May 25, 2006

Related U.S. Application Data

(60) Provisional application No. 60/630,399, filed on Nov. 19, 2004.

(51) Int. Cl.
*A61F 2/20* (2006.01)
(52) U.S. Cl. ...................... 623/9; 128/207.15
(58) Field of Classification Search ............. 623/9; 128/107.16–207.19; 606/108
See application file for complete search history.

(56) References Cited

U.S. PATENT DOCUMENTS

| | | | |
|---|---|---|---|
| 2,981,254 A | 4/1961 | Vanderbilt |
| 3,657,744 A | 4/1972 | Ersek |
| 3,667,069 A | 6/1972 | Blackshear et al. |
| 3,788,327 A | 1/1974 | Donowitz et al. |
| 3,874,388 A | 4/1975 | King et al. |
| 4,014,318 A | 3/1977 | Dockum et al. |
| 4,086,665 A | 5/1978 | Poirier |
| 4,212,463 A | 7/1980 | Repinski et al. |
| 4,250,873 A | 2/1981 | Bonnet |
| 4,302,854 A | 12/1981 | Runge |
| 4,477,930 A | 10/1984 | Totten et al. |

(Continued)

FOREIGN PATENT DOCUMENTS

DE     9205797.7     6/1992

(Continued)

OTHER PUBLICATIONS

Al Jishi et al., "Selective Bronchial Occlusion for Treatment of Bullous Interstitial Emphysema and Bronchopleural Fistula." *J. of Pediatric Surgery,* 29:1545-1547, 1994.

(Continued)

*Primary Examiner*—Suzette J Gherbi
(74) *Attorney, Agent, or Firm*—Townsend and Townsend and Crew LLP

(57) ABSTRACT

Disclosed is an assembly for loading a bronchial flow control device into a container, such as into a delivery catheter. The assembly includes a funnel housing and a puller housing that mate with one another. The funnel housing defines a funnel-shaped loading cavity that receives a flow control device and that gradually reduces in size moving in a first direction. The puller housing is removably attached to the funnel housing and is also removably attachable to a bronchial flow control device that can be positioned in the loading cavity. The puller housing pulls the bronchial flow control device in the first direction through the funnel housing to gradually contract the bronchial flow control device into a compressed state of reduced size relative to the expanded state.

14 Claims, 30 Drawing Sheets

U.S. PATENT DOCUMENTS

| | | | |
|---|---|---|---|
| 4,710,192 A | 12/1987 | Liotta et al. | |
| 4,732,152 A | 3/1988 | Wallsten et al. | |
| 4,759,758 A | 7/1988 | Gabbay | |
| 4,774,942 A | 10/1988 | Moellers | |
| 4,795,449 A | 1/1989 | Schneider et al. | |
| 4,808,183 A | 2/1989 | Panje | |
| 4,819,664 A | 4/1989 | Nazari | |
| 4,830,003 A | 5/1989 | Wolff et al. | |
| 4,832,680 A | 5/1989 | Haber et al. | |
| 4,846,836 A | 7/1989 | Reich | |
| 4,850,999 A | 7/1989 | Planck | |
| 4,852,568 A | 8/1989 | Kensey | |
| 4,877,025 A | 10/1989 | Hanson | |
| 4,879,998 A | 11/1989 | Moellers | |
| 4,934,999 A | 6/1990 | Bader | |
| 4,968,294 A | 11/1990 | Salama | |
| 4,990,151 A | 2/1991 | Wallstén | |
| 5,061,274 A | 10/1991 | Kensey | |
| 5,116,360 A | 5/1992 | Pinchuk et al. | |
| 5,116,564 A | 5/1992 | Jansen et al. | |
| 5,123,919 A | 6/1992 | Sauter et al. | |
| 5,151,105 A | 9/1992 | Kwan-Gett | |
| 5,158,548 A | 10/1992 | Lau et al. | |
| 5,161,524 A | 11/1992 | Evans | |
| 5,306,234 A | 4/1994 | Johnson | |
| 5,352,240 A | 10/1994 | Ross | |
| 5,358,518 A | 10/1994 | Camilli | |
| 5,366,478 A | 11/1994 | Brinkerhoff et al. | |
| 5,382,261 A | 1/1995 | Palmaz | |
| 5,392,775 A | 2/1995 | Adkins et al. | |
| 5,409,019 A | 4/1995 | Wilk | |
| 5,411,507 A | 5/1995 | Heckele | |
| 5,411,552 A | 5/1995 | Andersen et al. | |
| 5,413,599 A | 5/1995 | Imachi et al. | |
| 5,417,226 A | 5/1995 | Juma | |
| 5,445,626 A | 8/1995 | Gigante | |
| 5,453,090 A | 9/1995 | Martinez et al. | |
| 5,486,154 A | 1/1996 | Kelleher | |
| 5,499,995 A | 3/1996 | Teirstein | |
| 5,500,014 A | 3/1996 | Quijano et al. | |
| 5,522,881 A | 6/1996 | Lentz | |
| 5,562,608 A | 10/1996 | Sekins et al. | |
| 5,588,424 A | 12/1996 | Insler et al. | |
| 5,645,519 A | 7/1997 | Lee et al. | |
| 5,645,565 A | 7/1997 | Rudd et al. | |
| 5,649,906 A | 7/1997 | Gory et al. | |
| 5,660,175 A | 8/1997 | Dayal | |
| 5,662,713 A | 9/1997 | Andersen et al. | |
| 5,676,671 A | 10/1997 | Inoue | |
| 5,683,451 A | 11/1997 | Lenker et al. | |
| 5,697,968 A | 12/1997 | Rogers et al. | |
| 5,755,770 A | 5/1998 | Ravenscroft | |
| 5,800,339 A | 9/1998 | Salama | |
| 5,803,080 A | 9/1998 | Freitag | |
| 5,824,037 A | 10/1998 | Fogarty et al. | |
| 5,840,081 A | 11/1998 | Andersen et al. | |
| 5,843,158 A | 12/1998 | Lenker et al. | |
| 5,851,232 A | 12/1998 | Lois | |
| 5,855,587 A | 1/1999 | Hyon et al. | |
| 5,855,597 A | 1/1999 | Jayaraman | |
| 5,855,601 A | 1/1999 | Bessler et al. | |
| 5,868,779 A | 2/1999 | Ruiz | |
| 5,891,195 A | 4/1999 | Klostermeyre et al. | |
| 5,910,144 A | 6/1999 | Hayashi | |
| 5,944,738 A | 8/1999 | Amplatz et al. | |
| 5,947,997 A | 9/1999 | Pavcnik et al. | |
| 5,954,765 A | 9/1999 | Ruiz | |
| 5,954,766 A | 9/1999 | Zadno-Azizi et al. | |
| 5,957,949 A | 9/1999 | Leonhardt et al. | |
| 5,976,174 A | 11/1999 | Ruiz | |
| 5,980,455 A | 11/1999 | Daniel et al. | |
| 5,984,965 A | 11/1999 | Knapp et al. | |
| 5,989,288 A | 11/1999 | Pintauro et al. | |
| 6,007,575 A | 12/1999 | Samuels | |
| 6,009,614 A | 1/2000 | Morales | |
| 6,020,380 A | 2/2000 | Killian | |
| 6,022,312 A | 2/2000 | Chaussy et al. | |
| 6,027,508 A | 2/2000 | Ren et al. | |
| 6,027,525 A | 2/2000 | Suh et al. | |
| 6,051,022 A | 4/2000 | Cai et al. | |
| 6,068,635 A | 5/2000 | Gianotti | |
| 6,068,638 A | 5/2000 | Makower | |
| 6,077,291 A | 6/2000 | Das | |
| 6,083,255 A | 7/2000 | Laufer et al. | |
| 6,123,663 A | 9/2000 | Rebuffat | |
| 6,135,729 A | 10/2000 | Aber | |
| 6,135,991 A | 10/2000 | Muni et al. | |
| 6,141,855 A | 11/2000 | Morales | |
| 6,162,245 A | 12/2000 | Jayaraman | |
| 6,168,614 B1 | 1/2001 | Andersen et al. | |
| 6,174,323 B1 | 1/2001 | Biggs et al. | |
| 6,183,520 B1 | 2/2001 | Pintauro et al. | |
| 6,190,381 B1 | 2/2001 | Olsen et al. | |
| 6,200,333 B1 | 3/2001 | Laufer | |
| 6,206,918 B1 | 3/2001 | Campbell et al. | |
| 6,234,996 B1 | 5/2001 | Bagaoisan et al. | |
| 6,240,615 B1 | 6/2001 | Kimes et al. | |
| 6,245,102 B1 | 6/2001 | Jayaraman | |
| 6,247,471 B1 | 6/2001 | Bower et al. | |
| 6,258,100 B1 | 7/2001 | Alferness et al. | |
| 6,270,527 B1 | 8/2001 | Campbell et al. | |
| 6,280,464 B1 | 8/2001 | Hayashi | |
| 6,287,290 B1 | 9/2001 | Perkins et al. | |
| 6,293,951 B1 | 9/2001 | Alferness et al. | |
| 6,302,893 B1 | 10/2001 | Limon et al. | |
| 6,312,407 B1 | 11/2001 | Zadno-Azizi et al. | |
| 6,325,777 B1 | 12/2001 | Zadno-Azizi et al. | |
| 6,325,778 B1 | 12/2001 | Zadno-Azizi et al. | |
| 6,327,772 B1 | 12/2001 | Zadno-Azizi et al. | |
| 6,328,689 B1 | 12/2001 | Gonzalez | |
| 6,355,014 B1 | 3/2002 | Zadno-Azizi et al. | |
| 6,398,775 B1 | 6/2002 | Perkins et al. | |
| 6,402,754 B1 | 6/2002 | Gonzalez | |
| 6,416,554 B1 | 7/2002 | Alferness et al. | |
| 6,458,076 B1 | 10/2002 | Pruitt | |
| 6,485,407 B2 | 11/2002 | Alferness et al. | |
| 6,491,706 B1 | 12/2002 | Alferness et al. | |
| 6,493,589 B1 | 12/2002 | Medhkour et al. | |
| 6,510,846 B1 | 1/2003 | O'Rourke | |
| 6,527,761 B1 | 3/2003 | Soltesz et al. | |
| 6,558,318 B1 | 5/2003 | Daniel et al. | |
| 6,592,594 B2 | 7/2003 | Rimbaugh et al. | |
| 6,632,243 B1 | 10/2003 | Zadno-Azizi et al. | |
| 6,679,264 B1 | 1/2004 | Deem et al. | |
| 6,694,979 B2 | 2/2004 | Deem et al. | |
| 6,699,231 B1 | 3/2004 | Sterman et al. | |
| 6,837,906 B2 | 1/2005 | Ginn | |
| 6,840,243 B2 | 1/2005 | Deem et al. | |
| 6,840,957 B2 | 1/2005 | Di Matteo et al. | |
| 6,878,141 B1 | 4/2005 | Perkins et al. | |
| 6,901,927 B2 | 6/2005 | Deem et al. | |
| 6,904,909 B2 | 6/2005 | Andreas et al. | |
| 6,905,518 B2 | 6/2005 | Ginn | |
| 6,941,950 B2 * | 9/2005 | Wilson et al. | 128/207.14 |
| 7,011,094 B2 * | 3/2006 | Rapacki et al. | 128/207.15 |
| 2001/0025132 A1 | 9/2001 | Alferness et al. | |
| 2001/0037808 A1 | 11/2001 | Deem et al. | |
| 2001/0041906 A1 | 11/2001 | Gonzalez | |
| 2001/0051799 A1 | 12/2001 | Ingenito | |
| 2001/0052344 A1 | 12/2001 | Doshi | |
| 2001/0056274 A1 | 12/2001 | Perkins et al. | |
| 2002/0007831 A1 | 1/2002 | Davenport et al. | |
| 2002/0026233 A1 | 2/2002 | Shaknovich | |
| 2002/0062120 A1 | 5/2002 | Perkins et al. | |

| | | | | | |
|---|---|---|---|---|---|
| 2002/0077593 A1 | 6/2002 | Perkins et al. | WO | 96/39960 | 12/1996 |
| 2002/0077696 A1 | 6/2002 | Zadno-Azizi et al. | WO | 97/44085 | 11/1997 |
| 2002/0087153 A1 | 7/2002 | Roschak et al. | WO | 98/00840 | 1/1998 |
| 2002/0095209 A1 | 7/2002 | Zadno-Azizi et al. | WO | 98/19633 | 5/1998 |
| 2002/0111619 A1 | 8/2002 | Keast et al. | WO | 98/39047 | 9/1998 |
| 2002/0111620 A1 | 8/2002 | Cooper et al. | WO | 98/44854 | 10/1998 |
| 2002/0112729 A1 | 8/2002 | DeVore et al. | WO | 98/48706 | 11/1998 |
| 2002/0138135 A1 | 9/2002 | Duerig et al. | WO | 99/01076 | 1/1999 |
| 2003/0018327 A1 | 1/2003 | Truckai et al. | WO | 99/13801 | 3/1999 |
| 2003/0018344 A1 | 1/2003 | Kaji et al. | WO | 99/26692 | 6/1999 |
| 2003/0050648 A1 | 3/2003 | Alferness et al. | WO | 99/32040 | 7/1999 |
| 2003/0070682 A1 | 4/2003 | Wilson et al. | WO | 99/42059 | 8/1999 |
| 2003/0070683 A1 | 4/2003 | Deem et al. | WO | 99/42161 | 8/1999 |
| 2003/0075169 A1 | 4/2003 | Deem et al. | WO | 99/64109 | 12/1999 |
| 2003/0075170 A1 | 4/2003 | Deem et al. | WO | 00/15149 | 3/2000 |
| 2003/0083671 A1 | 5/2003 | Rimbaugh et al. | WO | 00/42950 | 7/2000 |
| 2003/0127090 A1 | 7/2003 | Gifford et al. | WO | 00/51510 | 9/2000 |
| 2003/0164168 A1 | 9/2003 | Shaw et al. | WO | 00/62699 | 10/2000 |
| 2003/0192550 A1 | 10/2003 | Deem et al. | WO | 00/78386 | 12/2000 |
| 2003/0192551 A1 | 10/2003 | Deem et al. | WO | 00/78407 | 12/2000 |
| 2003/0199972 A1 | 10/2003 | Zadno-Azizi et al. | WO | 01/02042 | 1/2001 |
| 2003/0212452 A1 | 11/2003 | Zadno-Azizi et al. | WO | 01/03642 | 1/2001 |
| 2003/0228344 A1 | 12/2003 | Fields et al. | WO | 01/05334 | 1/2001 |
| 2004/0016435 A1 | 1/2004 | Deem et al. | WO | 01/10313 | 2/2001 |
| 2004/0039250 A1 | 2/2004 | Tholfsen et al. | WO | 01/10314 | 2/2001 |
| 2004/0055606 A1 | 3/2004 | Hendricksen et al. | WO | 01/12104 | 2/2001 |
| 2004/0060563 A1 | 4/2004 | Rapacki et al. | WO | 01/13839 | 3/2001 |
| 2004/0074491 A1 | 4/2004 | Hendricksen et al. | WO | 01/13908 | 3/2001 |
| 2004/0089306 A1 | 5/2004 | Hundertmark et al. | WO | 01/45590 | 6/2001 |
| 2004/0134487 A1 | 7/2004 | Deem et al. | WO | 01/49213 | 7/2001 |
| 2004/0148035 A1 | 7/2004 | Barrett et al. | WO | 01/54585 | 8/2001 |
| 2004/0154621 A1 | 8/2004 | Deem et al. | WO | 01/54625 | 8/2001 |
| 2004/0194780 A1 | 10/2004 | Doshi | WO | 01/54685 | 8/2001 |
| 2004/0200484 A1 | 10/2004 | Springmeyer | WO | 01/66190 | 9/2001 |
| 2004/0211434 A1 | 10/2004 | Loomas et al. | WO | 01/74271 | 10/2001 |
| 2005/0005936 A1 | 1/2005 | Wondka | WO | 01/87170 | 11/2001 |
| 2005/0015106 A1 | 1/2005 | Perkins | WO | 01/89366 | 11/2001 |
| 2005/0016530 A1 | 1/2005 | McCutcheon et al. | WO | 01/95786 | 12/2001 |
| 2005/0022809 A1 | 2/2005 | Wondka | WO | 02/05884 | 1/2002 |
| 2005/0033310 A1 | 2/2005 | Alferness et al. | WO | 02/22072 | 3/2002 |
| 2005/0033344 A1 | 2/2005 | Dillard et al. | WO | 02/32333 | 4/2002 |
| 2005/0051163 A1 | 3/2005 | Deem et al. | WO | 02/34322 | 5/2002 |
| 2005/0061322 A1 | 3/2005 | Freitag | WO | 02/38038 | 5/2002 |
| 2005/0066974 A1 | 3/2005 | Fields et al. | WO | 02/47575 | 6/2002 |
| 2005/0087137 A1 | 4/2005 | Park et al. | WO | 02/056794 | 7/2002 |
| 2005/0125076 A1 | 6/2005 | Ginn | WO | 02/064045 | 8/2002 |
| 2005/0137714 A1 | 6/2005 | Gonzalez et al. | WO | 02/064190 | 8/2002 |
| 2005/0145253 A1* | 7/2005 | Wilson et al. .......... 128/207.14 | WO | 02/069823 | 9/2002 |
| 2005/0161048 A1 | 7/2005 | Rapacki et al. | WO | 02/094087 | 11/2002 |
| 2005/0166925 A1* | 8/2005 | Wilson et al. .......... 128/207.14 | WO | 03/022124 | 3/2003 |
| 2005/0171396 A1 | 8/2005 | Pankratov et al. | WO | 03/030975 | 4/2003 |
| 2005/0178389 A1 | 8/2005 | Shaw et al. | WO | 03/041779 | 5/2003 |
| 2005/0196344 A1 | 9/2005 | McCutcheon et al. | WO | 03/075796 | 9/2003 |
| 2005/0203483 A1 | 9/2005 | Perkins et al. | WO | 03/099164 | 12/2003 |
| 2006/0004305 A1* | 1/2006 | George et al. ............... 600/593 | WO | 2004/006767 | 1/2004 |
| 2006/0020347 A1* | 1/2006 | Barrett et al. ............ 623/23.65 | WO | 2004/010845 | 2/2004 |
| 2006/0030863 A1 | 2/2006 | Fields et al. | WO | 2004/049974 | 6/2004 |
| 2008/0072914 A1* | 3/2008 | Hendricksen et al. .. 128/207.16 | WO | 2004/080347 | 9/2004 |
| | | | WO | 2005/000161 | 1/2005 |
| | | | WO | 2005/006957 | 1/2005 |
| | | | WO | 2005/007023 | 1/2005 |
| | | | WO | 2005/013808 | 2/2005 |
| | | | WO | 2005/013835 | 2/2005 |
| | | | WO | 2005/087137 | 9/2005 |

FOREIGN PATENT DOCUMENTS

| | | |
|---|---|---|
| EP | 0 621 015 | 10/1994 |
| EP | 1 078 601 | 2/2001 |
| EP | 0 128 433 | 4/2001 |
| EP | 1 151 729 | 11/2001 |
| GB | 2324729 | 4/1998 |
| RU | 2140211 | 10/1999 |
| SU | 852321 | 7/1981 |
| SU | 1371700 | 2/1988 |
| SU | 1593651 | 9/1990 |
| WO | 94/26175 | 11/1994 |
| WO | 95/32018 | 11/1995 |
| WO | 96/34582 | 11/1996 |

OTHER PUBLICATIONS

Article: "Autocath® 100—Nonsurgical, Intraurethral Bladder Control Device for Incontinent and Retentive Women—Dr. Kulisz's Development".

Certified English Translation of German patent G 92 05 797.7, published Jul. 30, 1993, entitled "Self-expanding mesh basket used to occlude human hollow organs".

Certified English Translation of USSR patent 852321, published Aug. 7, 1981, entitled "A Method of Treatment of Acute Purulent Diseases of the Lungs and Pleura in Children".

Derwent citing Russian Patent No. RU 2140211, published Oct. 27, 1999, for: "Method of surgical treatment of patients with pathology of respiratory organs complicated with pulmonary hemorrhages".

Derwent citing Soviet Union Patent No. SU 852-321, published Jul. 8, 1981, for: "Treatment for acute pulmonary and pleural disease in children—by pneumo-abcessotomy simultaneous with occlusion of affected lung part".

Derwent# 007607249 WPI Acc. No. 1988-241181/198834 (citing Russian Application No. SU4026409, published Feb. 21, 1986), Russian Patent No. SU 1371700.

Derwent# 008650867 WPI Acc. No. 1991-154896/199121 (citing Russian Application No. SU4280143, published Jul. 7, 1987), Russian Patent No. SU 1593651.

Harris et al., "The Experimental Production in Dogs of Emphysema with Associated Asthmatic Syndrome by Means of an Intratracheal Ball Valve", *J. Lab. Clini. Med.*, 9(iv):75-88, 1919.

Lewis et al., "Pulmonary Interstitial Emphysema: Selective Broncial Occlusion with a Swan-Ganz Catheter", *Archives of Disease in Childhood*, 63:313-315, 1988.

Mathew et al., "Selective bronchial obstruction for treatment of bullous interstitial emphysema." *J. of Ped.*, 96:475-477, 1980.

Okada et al., "Emergent Bronchofiberoptic Bronchial Occlusion for Intractable Pneumothorax with Severe Emphysema", *The Jap. J. of Thor. And Cardio. Sur.*, 46:1078-1081, 1998.

Puhakka et al., "Acute Bronchial Obstruction: An Experimental Rabbit Model Study", *Int. J. of Pediatric Otorhinolaryngology*, 18:107-118, 1989.

Snider et al., *The Definition of Emphysema:* Report of the National Heart Lung and Blood Institute, Division of Lung Diseases Workshop, *Am. Rev. Respir. Dis.*, 132:182-185, 1985.

Woodring et al., "Pneumothorax ex Vacuo", *CHEST*, 100:1102-1105, 1996.

\* cited by examiner

BRONCHIAL FLOW CONTROL DEVICES AND METHODS OF USE

REFERENCE TO PRIORITY DOCUMENT

This application claims priority of co-pending U.S. Provisional Patent Application Ser. No. 60/630,399 entitled "Bronchial Flow Control Devices and Methods of Use", filed Nov. 19, 2004. Priority of the aforementioned filing date is hereby claimed, and the disclosure of the Provisional Patent Application is hereby incorporated by reference in its entirety.

BACKGROUND

Pulmonary diseases, such as chronic obstructive pulmonary disease, (COPD), reduce the ability of one or both lungs to fully expel air during the exhalation phase of the breathing cycle. Such diseases are accompanied by chronic or recurrent obstruction to air flow within the lung. Because of the increase in environmental pollutants, cigarette smoking, and other noxious exposures, the incidence of COPD has increased dramatically in the last few decades and now ranks as a major cause of activity-restricting or bed-confining disability in the United States. COPD can include such disorders as chronic bronchitis, bronchiectasis, asthma, and emphysema.

It is known that emphysema and other pulmonary diseases reduce the ability of one or both lungs to fully expel air during the exhalation phase of the breathing cycle. One of the effects of such diseases is that the diseased lung tissue is less elastic than healthy lung tissue, which is one factor that prevents full exhalation of air. During breathing, the diseased portion of the lung does not fully recoil due to the diseased (e.g., emphysematic) lung tissue being less elastic than healthy tissue. Consequently, the diseased lung tissue exerts a relatively low driving force, which results in the diseased lung expelling less air volume than a healthy lung. The reduced air volume exerts less force on the airway, which allows the airway to close before all air has been expelled, another factor that prevents full exhalation.

The problem is further compounded by the diseased, less elastic tissue that surrounds the very narrow airways that lead to the alveoli, which are the air sacs where oxygen-carbon dioxide exchange occurs. The diseased tissue has less tone than healthy tissue and is typically unable to maintain the narrow airways open until the end of the exhalation cycle. This traps air in the lungs and exacerbates the already-inefficient breathing cycle. The trapped air causes the tissue to become hyper-expanded and no longer able to effect efficient oxygen-carbon dioxide exchange.

In addition, hyper-expanded, diseased lung tissue occupies more of the pleural space than healthy lung tissue. In most cases, a portion of the lung is diseased while the remaining part is relatively healthy and, therefore, still able to efficiently carry out oxygen exchange. By taking up more of the pleural space, the hyper-expanded lung tissue reduces the amount of space available to accommodate the healthy, functioning lung tissue. As a result, the hyper-expanded lung tissue causes inefficient breathing due to its own reduced functionality and because it adversely affects the functionality of adjacent healthy tissue.

Some recent treatments include the use of devices that isolate a diseased region of the lung in order to reduce the volume of the diseased region, such as by collapsing the diseased lung region. According to such treatments, a delivery catheter is used to implant one or more flow control devices in airways feeding a diseased region of the lung to regulate fluid flow to the diseased lung region in order to fluidly isolate the region of the lung. These implanted flow control devices can be, for example, one-way valves that allow flow in the exhalation direction only, occluders or plugs that prevent flow in either direction, or two-way valves that control flow in both directions.

The flow control device is radially compressed into a contracted size for loading into the delivery catheter or a container associated with the catheter. It can be difficult to properly compress the flow control device to a size small enough to fit in the delivery catheter. Thus, there is a need for devices for properly compressing and loading a flow control device into a container or a delivery catheter.

SUMMARY

Disclosed are methods and bronchial flow control devices for regulating fluid flow to and from a region of a patient's lung, such as to achieve a desired fluid flow dynamic to a lung region during respiration and/or to induce collapse in one or more lung regions.

In one aspect, there is disclosed an assembly for loading a bronchial flow control device into a container. The assembly comprises a funnel housing and a puller housing. The funnel housing defines an internal, funnel-shaped loading cavity that gradually reduces in size moving in a first direction. The loading cavity is sized to receive a bronchial flow control device in an expanded state. The puller housing is removably attached to the funnel housing and is also removably attachable to a bronchial flow control device that can be positioned in the loading cavity. The puller housing pulls the bronchial flow control device in the first direction through the funnel housing to gradually contract the bronchial flow control device into a compressed state of reduced size relative to the expanded state.

In another aspect, there is disclosed an assembly for loading a bronchial flow control device into a container. The assembly comprises a funnel housing defining an internal, funnel-shaped loading cavity that gradually reduces in size moving in a first direction, wherein the loading cavity sized to receive a bronchial flow control device in an expanded state; a bronchial flow control device positioned in the loading cavity, the bronchial flow control device configured for placement in a bronchial passageway to regulate fluid flow through the bronchial passageway, and configured to form a seal with an interior wall of the bronchial passageway; a puller housing removably attached to the funnel housing; and a pulling structure removably attaching the puller housing to the bronchial flow control device. The puller housing and the puller structure pull the bronchial flow control device in the first direction through the funnel housing to gradually contract the bronchial flow control device into a compressed state of reduced size relative to the expanded state.

In another aspect, there is disclosed A bronchial flow control device assembly, comprising a funnel housing, a bronchial flow control device, and a puller housing. The funnel housing has an internal loading cavity and an internal transfer cavity, the loading cavity being funnel-shaped and having an outer dimension that gradually reduces from a large sized to a small size. The transfer cavity communicates with a first end of the loading cavity and has an outer dimension that is substantially equal to the small size of the loading cavity. The bronchial flow control device is positioned in the loading cavity while in an expanded state and is configured for placement in a bronchial passageway to regulate fluid flow through the bronchial passageway. The puller housing is removably connected to the funnel housing in a sliding fashion. The puller housing has a puller structure that connects the puller housing to at least a portion of the bronchial flow control device. The puller housing slidably disconnects from the funnel housing such that the puller structure pulls the bronchial flow control device through the loading cavity and into the transfer cavity such that the bronchial flow control device is contracted into a compressed state when positioned in the transfer cavity.

Other features and advantages should be apparent from the following description of various embodiments, which illustrate, by way of example, the principles of the invention.

BRIEF DESCRIPTION OF THE DRAWINGS

FIG. 30 shows a flow control device with suture loops attached to a suture attachment bar of the loader system of FIG. 26.

DETAILED DESCRIPTION

Disclosed are methods and devices for regulating fluid flow to and from a region of a patient's lung, such as to achieve a desired fluid flow dynamic to a lung region during respiration and/or to induce collapse in one or more lung regions. Also disclosed are methods and devices for loading a bronchial flow control device into a container or a catheter for delivering the bronchial flow control device to a bronchial passageway.

An identified region of the lung (referred to herein as the "targeted lung region") is targeted for treatment, such as to modify the air flow to the targeted lung region or to achieve volume reduction or collapse of the targeted lung region. The targeted lung region is then bronchially isolated to regulate airflow into and/or out of the targeted lung region through one or more bronchial passageways that feed air to the targeted lung region.

Figure 1:
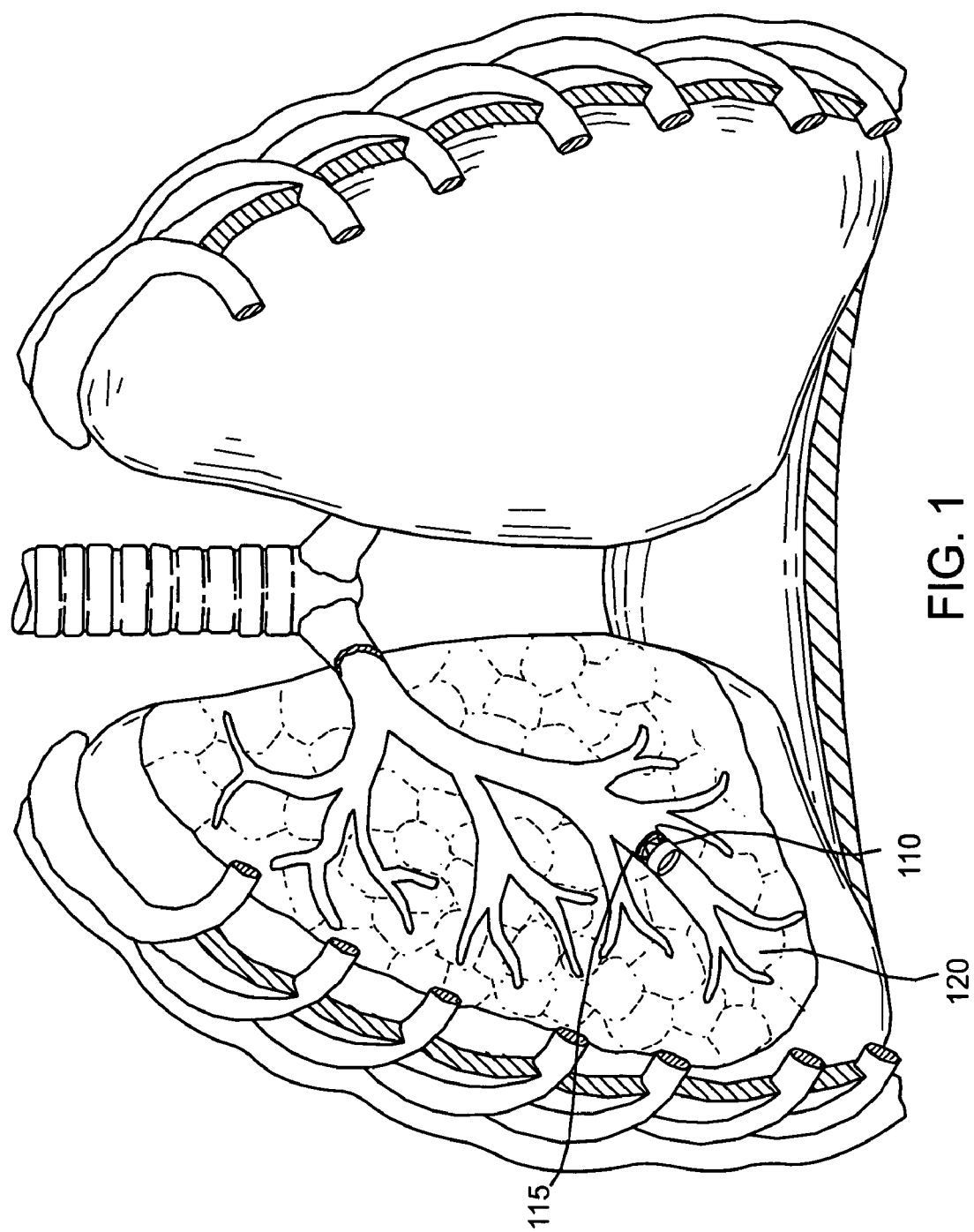
FIG. 1 shows an anterior view of a pair of human lungs and a bronchial tree with a flow control device implanted in a bronchial passageway to bronchially isolate a region of the lung.

As shown in FIG. 1, the bronchial isolation of the targeted lung region is accomplished by implanting a flow control device 110 into a bronchial passageway 115 that feeds air to a targeted lung region 120. The flow control device 110 regulates airflow through the bronchial passageway 115 in which the flow control device 110 is implanted, as described in more detail below. The flow control device 110 can be implanted into the bronchial passageway using a delivery system, such as the delivery system catheter described herein. As described below, a loader device is used to compress the size of the flow control device and load the flow control device 110 into a container or a catheter for delivery into the lung.

Exemplary Lung Regions

Throughout this disclosure, reference is made to the term "lung region". As used herein, the term "lung region" refers to a defined division or portion of a lung. For purposes of example, lung regions are described herein with reference to human lungs, wherein some exemplary lung regions include lung lobes and lung segments. Thus, the term "lung region" as used herein can refer, for example, to a lung lobe or a lung segment. Such nomenclature conform to nomenclature for portions of the lungs that are known to those skilled in the art. However, it should be appreciated that the term "lung region" does not necessarily refer to a lung lobe or a lung segment, but can refer to some other defined division or portion of a human or non-human lung.

Figure 2:
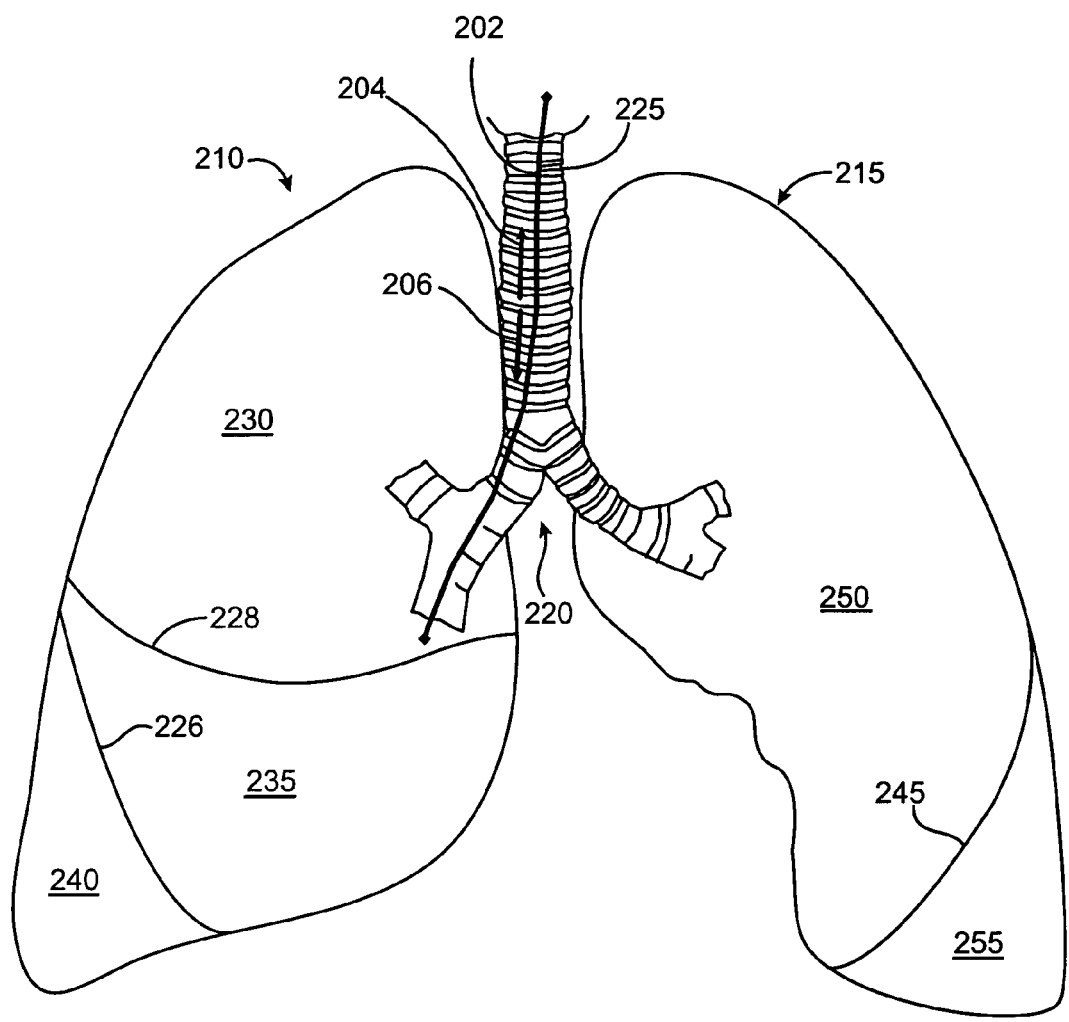
FIG. 2 illustrates an anterior view of a pair of human lungs and a bronchial tree.
Figure 5A:
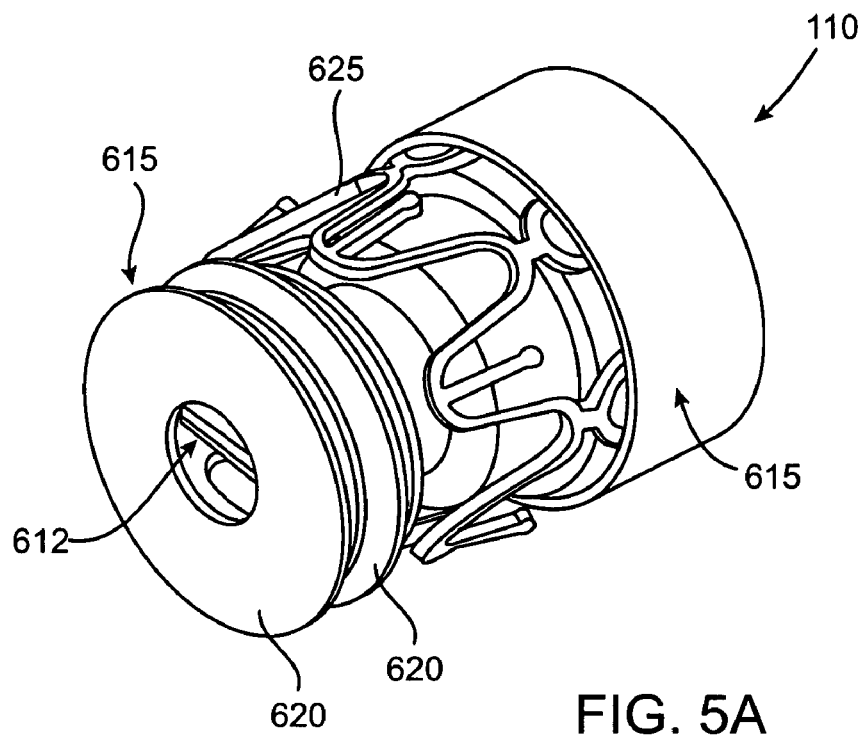
FIG. 5A shows a perspective view of an exemplary flow control device that can be implanted in a body passageway.

FIG. 2 shows an anterior view of a pair of human lungs 210, 215 and a bronchial tree 220 that provides a fluid pathway into and out of the lungs 210, 215 from a trachea 225, as will be known to those skilled in the art. As used herein, the term "fluid" can refer to a gas, a liquid, or a combination of gas(es) and liquid(s). For clarity of illustration, FIG. 2 shows only a portion of the bronchial tree 220, which is described in more detail below with reference to FIG. 5.

Throughout this description, certain terms are used that refer to relative directions or locations along a path defined from an entryway into the patient's body (e.g., the mouth or nose) to the patient's lungs. The path of airflow into the lungs generally begins at the patient's mouth or nose, travels through the trachea into one or more bronchial passageways, and terminates at some point in the patient's lungs. For example, FIG. 2 shows a path 202 that travels through the trachea 225 and through a bronchial passageway into a location in the right lung 210. The term "proximal direction" refers to the direction along such a path 202 that points toward the patient's mouth or nose and away from the patient's lungs. In other words, the proximal direction is generally the same as the expiration direction when the patient breathes. The arrow 204 in FIG. 2 points in the proximal or expiratory direction. The term "distal direction" refers to the direction along such a path 202 that points toward the patient's lung and away from the mouth or nose. The distal direction is generally the same as the inhalation or inspiratory direction when the patient breathes. The arrow 206 in FIG. 2 points in the distal or inhalation direction.

The lungs include a right lung 210 and a left lung 215. The right lung 210 includes lung regions comprised of three lobes, including a right upper lobe 230, a right middle lobe 235, and a right lower lobe 240. The lobes 230, 235, 240 are separated by two interlobar fissures, including a right oblique fissure 226 and a right transverse fissure 228. The right oblique fissure 226 separates the right lower lobe 240 from the right upper lobe 230 and from the right middle lobe 235. The right transverse fissure 228 separates the right upper lobe 230 from the right middle lobe 235.

As shown in FIG. 2, the left lung 215 includes lung regions comprised of two lobes, including the left upper lobe 250 and the left lower lobe 255. An interlobar fissure comprised of a left oblique fissure 245 of the left lung 215 separates the left upper lobe 250 from the left lower lobe 255. The lobes 230, 235, 240, 250, 255 are directly supplied air via respective lobar bronchi, as described in detail below.

Figure 3A:
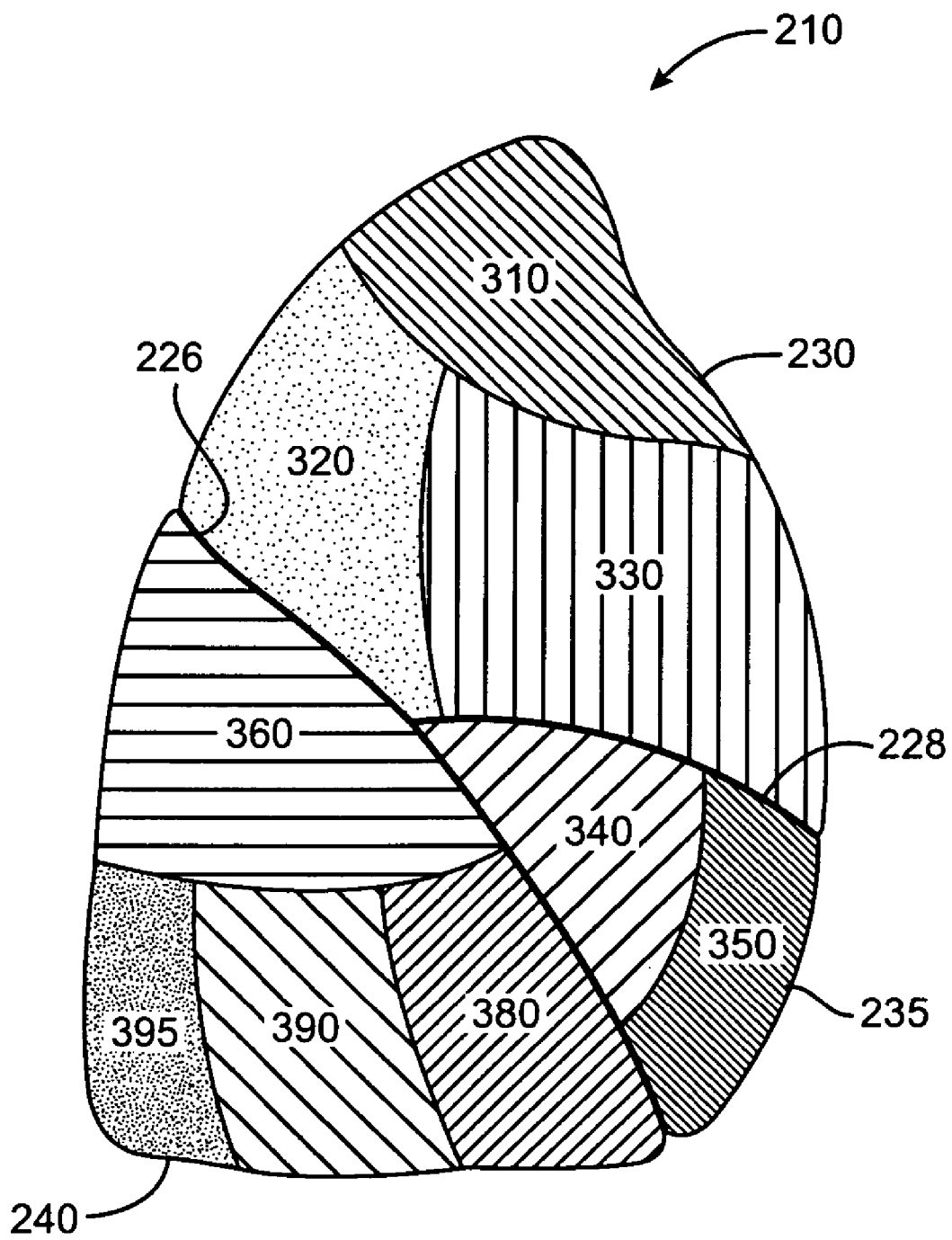
FIG. 3A illustrates a lateral view of the right lung.

FIG. 3A is a lateral view of the right lung 210. The right lung 210 is subdivided into lung regions comprised of a plurality of bronchiopulmonary segments. Each bronchiopulmonary segment is directly supplied air by a corresponding segmental tertiary bronchus, as described below. The bronchiopulmonary segments of the right lung 210 include a right apical segment 310, a right posterior segment 320, and a right anterior segment 330, all of which are disposed in the right upper lobe 230. The right lung bronchiopulmonary segments further include a right lateral segment 340 and a right medial segment 350, which are disposed in the right middle lobe 235. The right lower lobe 240 includes bronchiopulmonary segments comprised of a right superior segment 360, a right medial basal segment (which cannot be seen from the lateral view and is not shown in FIG. 3A), a right anterior basal segment 380, a right lateral basal segment 390; and a right posterior basal segment 395.

Figure 3B:
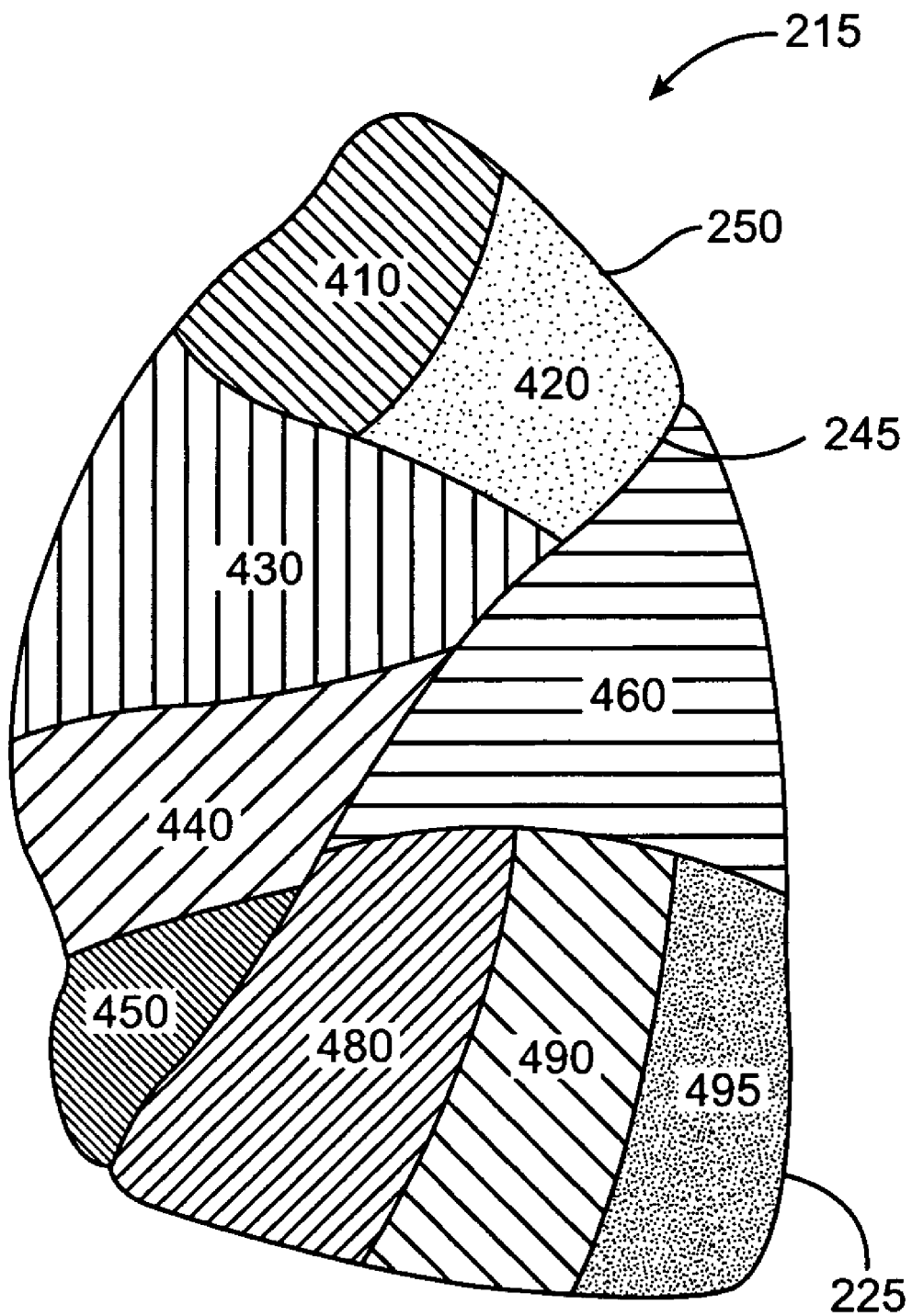
FIG. 3B illustrates a lateral view of the left lung.

FIG. 3B shows a lateral view of the left lung 215, which is subdivided into lung regions comprised of a plurality of bronchiopulmonary segments. The bronchiopulmonary segments include a left apical segment 410, a left posterior segment 420, a left anterior segment 430, a left superior segment 440, and a left inferior segment 450, which are disposed in the left lung upper lobe 250. The lower lobe 225 of the left lung 215 includes bronchiopulmonary segments comprised of a left superior segment 460, a left medial basal segment (which cannot be seen from the lateral view and is not shown in FIG. 3B), a left anterior basal segment 480, a left lateral basal segment 490, and a left posterior basal segment 495.

Figure 4:
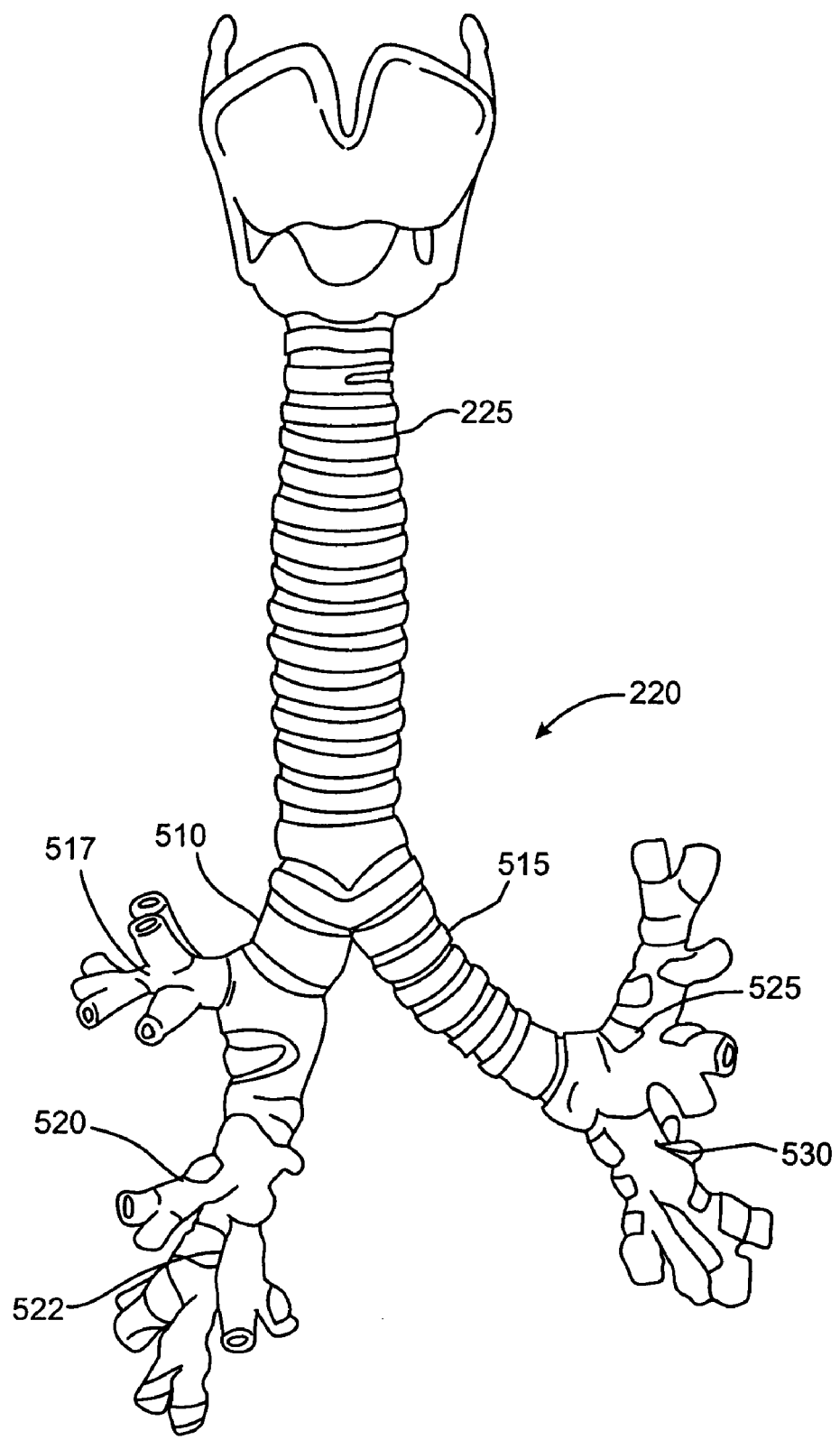
FIG. 4 illustrates an anterior view of the trachea and a portion of the bronchial tree.

FIG. 4 shows an anterior view of the trachea 225 and a portion of the bronchial tree 220, which includes a network of bronchial passageways, as described below. In the context of describing the lung, the terms "pathway" and "lumen" are used interchangeably herein. The trachea 225 divides at a lower end into two bronchial passageways comprised of primary bronchi, including a right primary bronchus 510 that provides direct air flow to the right lung 210, and a left primary bronchus 515 that provides direct air flow to the left lung 215. Each primary bronchus 510, 515 divides into a next generation of bronchial passageways comprised of a plurality of lobar bronchi. The right primary bronchus 510 divides into a right upper lobar bronchus 517, a right middle lobar bronchus 520, and a right lower lobar bronchus 522. The left primary bronchus 515 divides into a left upper lobar bronchus 525 and a left lower lobar bronchus 530. Each lobar bronchus, 517, 520, 522, 525, 530 directly feeds fluid to a respective lung lobe, as indicated by the respective names of the lobar bronchi. The lobar bronchi each divide into yet another generation of bronchial passageways comprised of segmental bronchi, which provide air flow to the bronchiopulmonary segments discussed above.

As is known to those skilled in the art, a bronchial passageway defines an internal lumen through which fluid can flow to and from a lung or lung region. The diameter of the internal lumen for a specific bronchial passageway can vary based on the bronchial passageway's location in the bronchial tree (such as whether the bronchial passageway is a lobar bronchus or a segmental bronchus) and can also vary from patient to patient. However, the internal diameter of a bronchial passageway is generally in the range of 3 millimeters (mm) to 10 mm, although the internal diameter of a bronchial passageway can be outside of this range. For example, a bronchial passageway can have an internal diameter of well below 1 mm at locations deep within the lung.

Flow Control Devices

FIGS. 5A-6B show an exemplary embodiment of a flow control device 110 that generally includes a valve, a frame or anchor, and a seal member for sealing against a wall of a bronchial passageway. It should be appreciated that the flow control device 110 shown in FIGS. 5A-6B is exemplary and that the frame, seal member, and valve can vary in structure. For example, the valve does not have to be configured with a central opening for fluid flow. Rather, the valve can be configured to interact with the walls of the bronchial passageway to permit or block fluid flow in that the valves contact or withdraw from the bronchial walls to block or permit fluid flow. The flow control device 110 has a general outer shape and contour that permits the flow control device 110 to fit entirely or at least partially within a body passageway, such as within a bronchial passageway.

The valve is configured to regulate fluid flow through a bronchial passageway in which the device 110 is implanted. The valve opens and vents fluid (such as gas or liquid, including mucous) when the pressure across the valve due to flow in a first direction, such as the exhalation direction, exceeds the rated cracking pressure of the valve. Thus, the valve opens in response to fluid flow in the first direction. The valve moves towards a closed configuration in response to fluid flow in a second, opposite direction such as the inhalation direction.

Figure 5B:
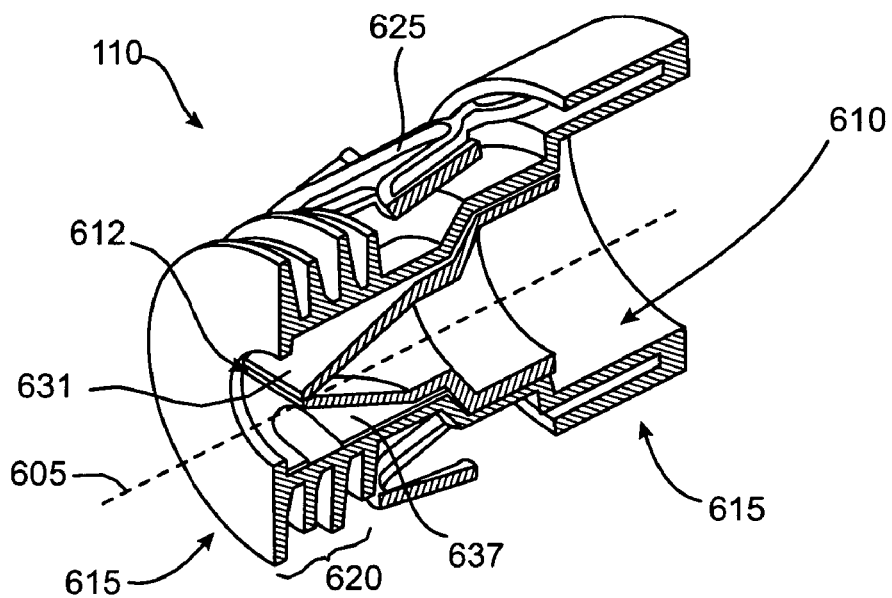
FIG. 5B shows a perspective, cross-sectional view of the flow control device of FIG. 5A.
Figure 6A:
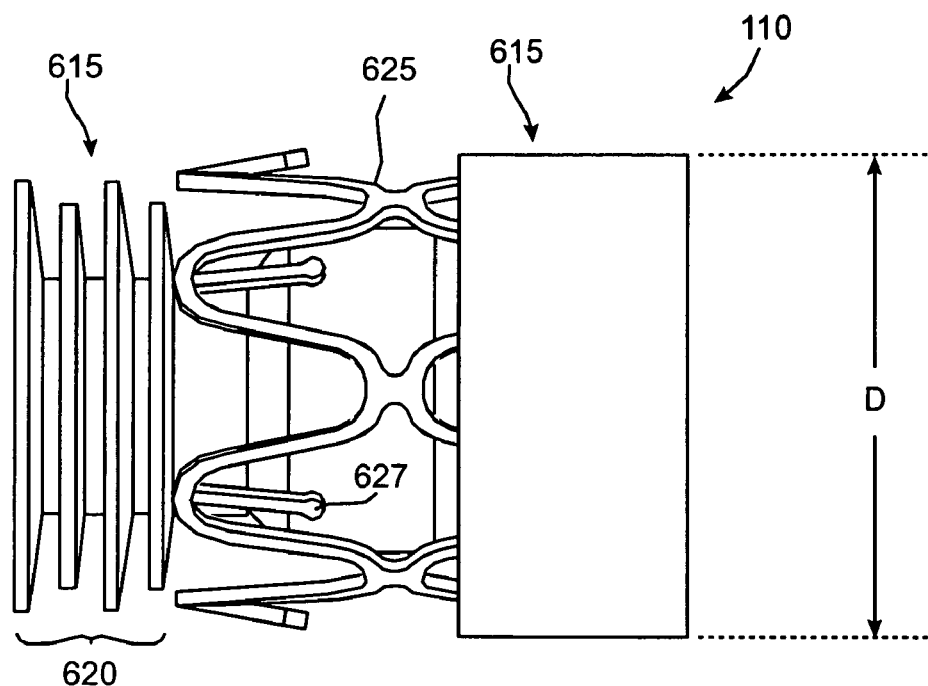
FIG. 6A shows a side view of the flow control device of FIG. 5A.
Figure 6B:
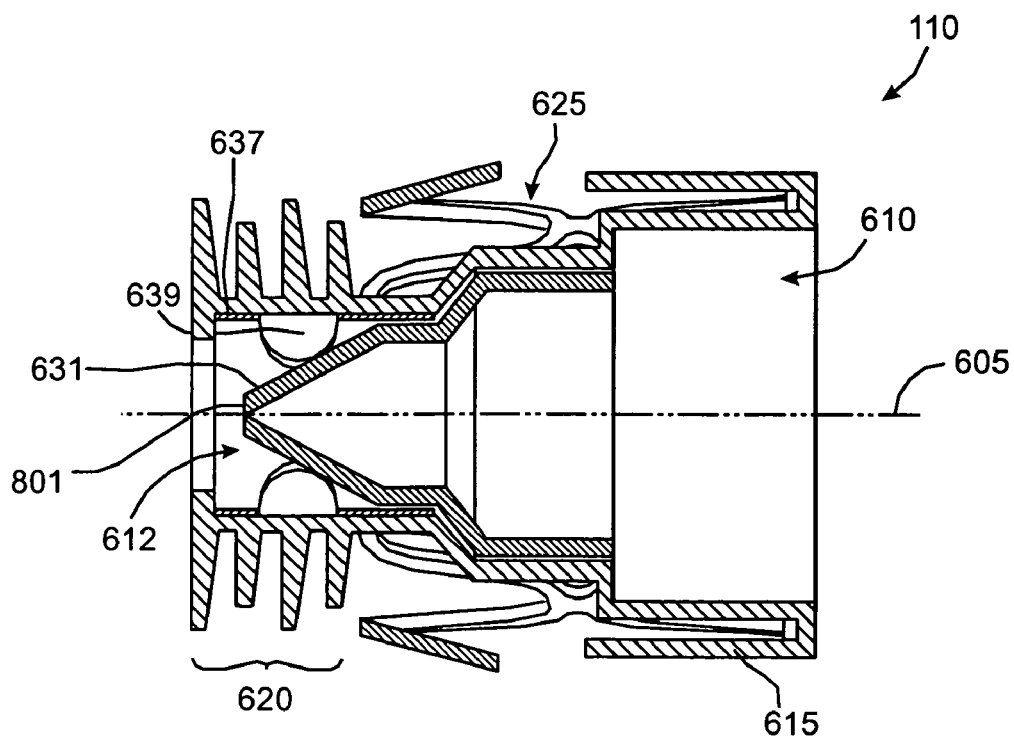
FIG. 6B shows a cross-sectional, side view of the flow control device of FIG. 5A.

With reference to FIGS. 5A-6B, the flow control device 110 extends generally along a central axis 605 (shown in FIGS. 5B and 6B). The flow control device 110 includes a main body that defines an interior lumen 610 through which fluid can flow along a flow path. The dimensions of the flow control device 110 can vary based upon the bronchial passageway in which the flow control device 110 is configured to be implanted. The valve does not have to be precisely sized for the bronchial passageway it is to be placed within. Generally, the diameter D (shown in FIG. 6A) of the flow control device 110 in the uncompressed state is larger than the inner diameter of the bronchial passageway in which the flow control device 110 will be placed. This will permit the flow control device 110 to be compressed prior to insertion in the bronchial passageway and then expand upon insertion in the bronchial passageway, which will provide for a secure fit between the flow control device 110 and the bronchial passageway.

The flow of fluid through the interior lumen 610 is controlled by a valve 612 that is disposed at a location along the interior lumen such that fluid must flow through the valve 612 in order to flow through the interior lumen 610. It should be appreciated that the valve 612 could be positioned at various locations along the interior lumen 610. The valve 612 can be made of a biocompatible material, such as a biocompatible polymer, such as silicone. As discussed in more detail below, the configuration of the valve 612 can vary based on a variety of factors, such as the desired cracking pressure of the valve 612.

The valve 612 can be configured to permit fluid to flow in only one-direction through the interior lumen 610, to permit regulated flow in two-directions through the interior lumen 610, or to prevent fluid flow in either direction.

With reference still to FIGS. 5A-6B, the flow control device 110 includes a seal member 615 that provides a seal with the internal walls of a body passageway when the flow control device is implanted into the body passageway. The seal member 615 is manufactured of a deformable material, such as silicone or a deformable elastomer. The flow control device 110 also includes an anchor member or frame 625 that functions to anchor the flow control device 110 within a body passageway.

As shown in FIGS. 5A-6B, the seal member 615 can includes a series of radially-extending, circular flanges 620 that surround the outer circumference of the flow control device 110. The configuration of the flanges can vary. For example, as shown in FIG. 6B, the radial length of each flange 620 can vary. It should be appreciated that the radial length could be equal for all of the flanges 620 or that the radial length of each flange could vary in some other manner. In addition, the flanges 620 can be oriented at a variety of angles relative to the longitudinal axis 605 of the flow control device.

As mentioned, the anchor member 625 functions to anchor the flow control device 110 in place when the flow control device is implanted within a body passageway, such as within a bronchial passageway. The anchor member 625 has a structure that can contract and expand in size (in a radial direction and/or in a longitudinal direction) so that the anchor member can expand to grip the interior walls of a body passageway in which the flow control device is positioned. In one embodiment, as shown in FIGS. 5A-6B, the anchor member 625 comprises an annular frame that surrounds the flow control device 110.

The frame 625 can be formed from a super-elastic material, such as Nickel Titanium (also known as Nitinol), such as by cutting the frame out of a tube of Nitinol or by forming the frame out of Nitinol wire. The super-elastic properties of Nitinol can result in the frame exerting a radial force against the interior walls of a bronchial passageway sufficient to anchor the flow control device 110 in place.

It should be appreciated that the configurations, including the sizes and shapes, of the frame 625 and the seal member 615 can vary from those shown in the figures. The seal 615 and/or the frame 625 can contract or expand in size, particularly in a radial direction. The default state is an expanded size, such that the flow control device 110 will have a maximum diameter (which is defined by either the seal 615 or the frame 625) when the flow control device 110 is in the default state. The flow control device 110 can be radially contracted in size during insertion into a bronchial passageway, so that once the flow control device 110 is inserted into the passageway, it expands within the passageway.

At least a portion of the valve 612 is optionally surrounded by a rigid or semi-rigid valve protector member 637 (shown in FIGS. 5B and 6B), which is a tubular member or annular wall that is contained inside the seal member 615. In another embodiment, the valve protector can comprise a coil of wire or a ring of wire that provides some level of structural support to the flow control device. The valve protector 637 can be concentrically located within the seal member 615. Alternately, the valve 612 can be completely molded within the seal member 615 such that the material of the seal member 615 completely surrounds the valve protector. The valve protector has sufficient rigidity to maintain the shape of the valve member against compression.

In one embodiment, the valve protector member 637 has two or more windows 639 comprising holes that extend through the valve protector member, as shown in FIG. 6B. The windows 639 can provide a location where a removal device, such as graspers or forceps, can be inserted in order to facilitate removal of the flow control device 110 from a bronchial passageway.

Figure 7:
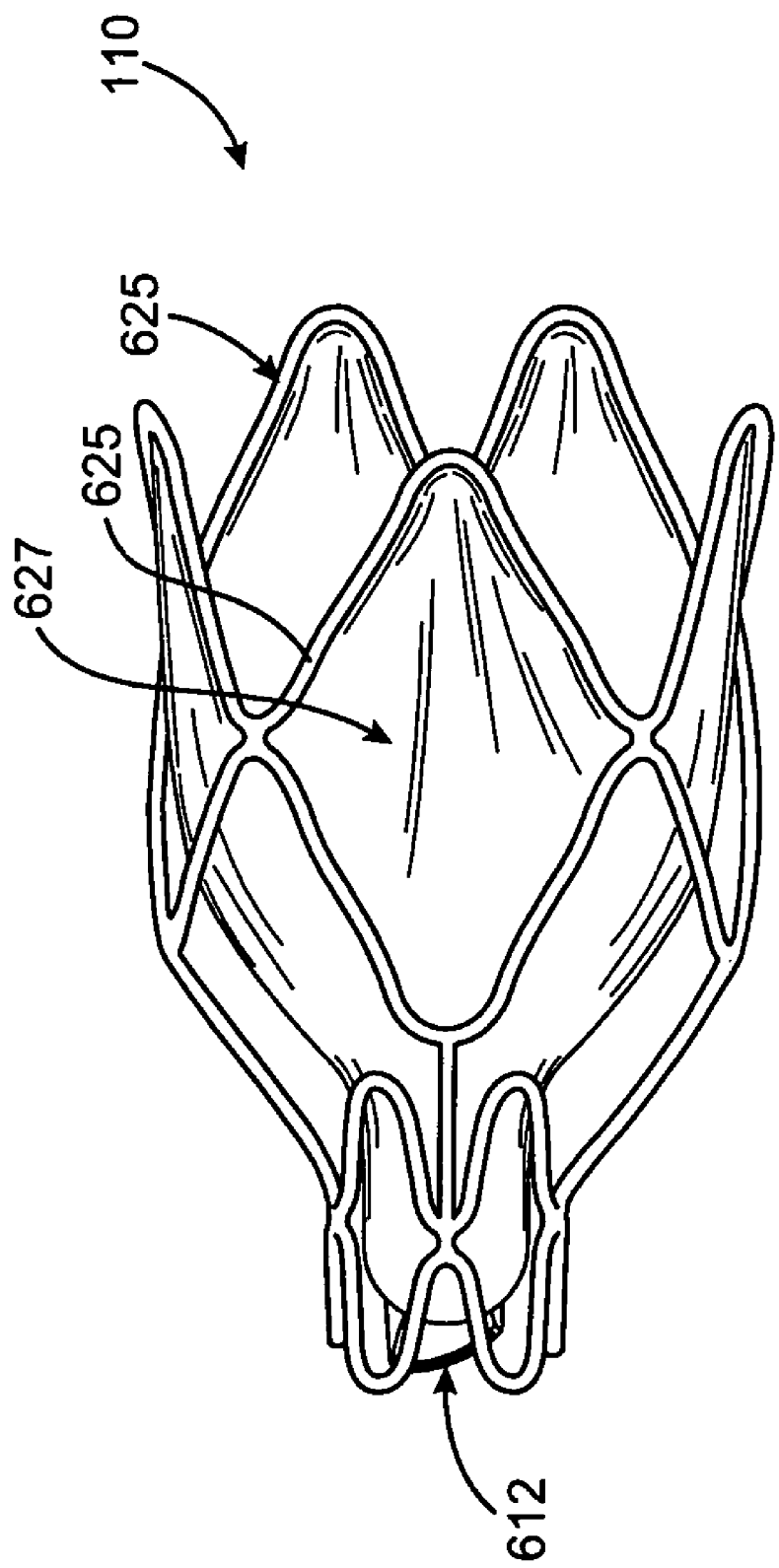
FIG. 7 shows another embodiment of a flow control device.

As mentioned, the structural configuration of the flow control device can vary. For example, FIG. 7 shows a perspective view of another embodiment of a flow control device 110 that includes a frame 625, a valve 612 mounted in the frame 625, and a membrane 627. The frame 625 and the membrane 627 can collectively or individually seal with an internal wall of a bronchial passageway.

Delivery System

Figure 8:
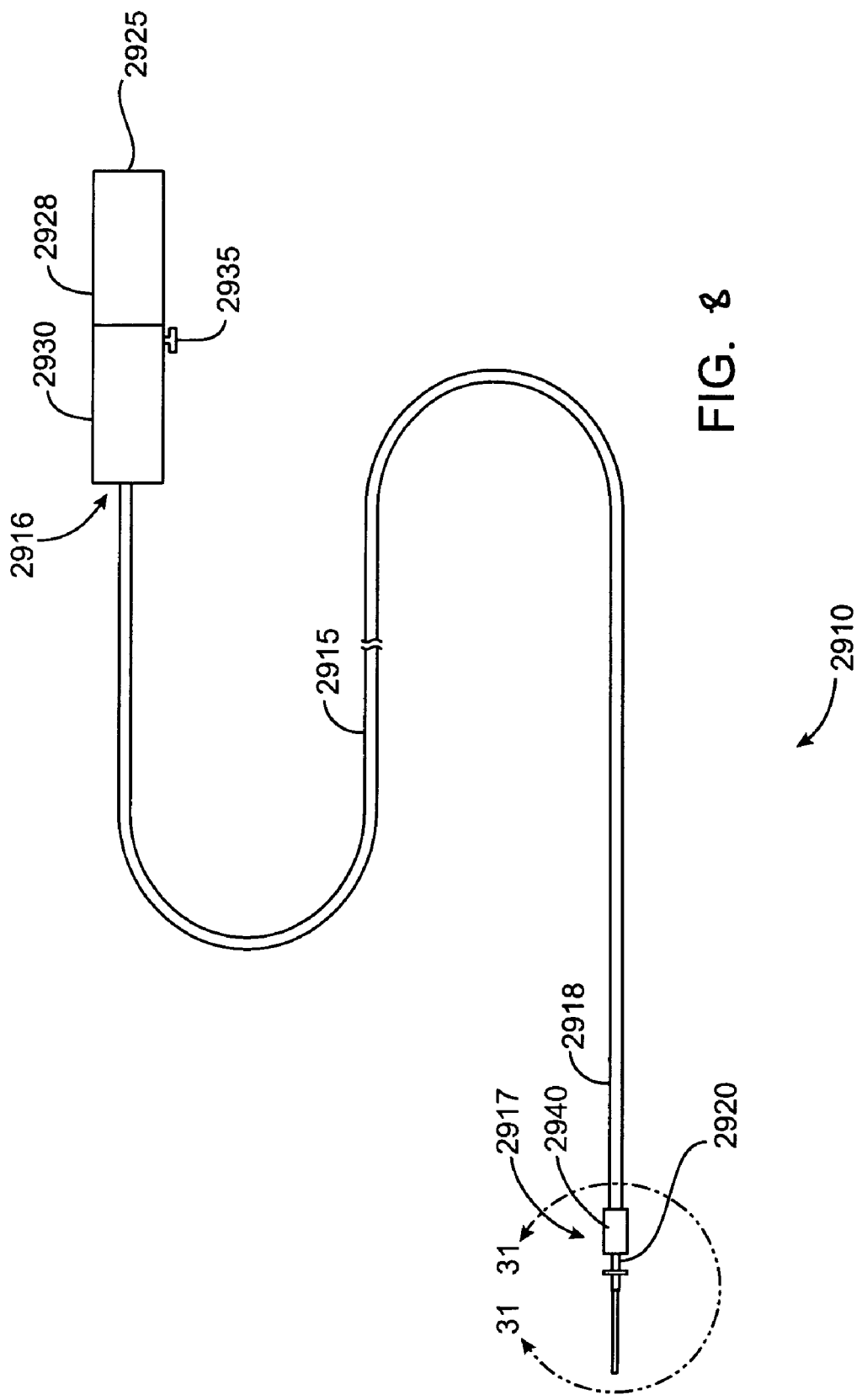
FIG. 8 shows a delivery system for delivering a flow control device to a target location in a body passageway.

FIG. 8 shows a delivery system 2910 for delivering and deploying a flow control device 110 to a target location in a bronchial passageway. The delivery system 2910 includes a catheter 2915 having a proximal end 2916, and a distal end 2917 that can be deployed to a target location in a patient's bronchial passageway, such as through the trachea. The catheter 2915 has an outer member 2918 and an inner member 2920 that is slidably positioned within the outer member 2918 such that the inner member 2920 can slidably move relative to the outer member 2918 along the length of the catheter 2915.

In this regard, an actuation member, such as a two-piece handle 2925, is located at the proximal end 2916 of the catheter 2915. The handle 2925 can be actuated to move the inner member 2920 relative to the outer member 2918 (and vice-versa). In the illustrated embodiment, the handle 2925 includes a first piece 2928 and a second piece 2930, which is slidably moveable with respect to the first piece 2928. The inner member 2920 of the catheter 2915 can be moved relative to the outer member 2918 by slidably moving the first piece 2928 of the handle 2925 relative to the second piece 2930. The actuation member could also take on other structural forms that use other motions to move the inner member 2920 relative to the outer member 2918. For example, the actuation member could have scissor-like handles or could require a twisting motion to move the inner member 2920 relative to the outer member 2918.

As shown in FIG. 8, the handle 2925 also includes a locking mechanism 2935 for locking the position of the first piece 2928 relative to the second piece 2930 to thereby lock the position of the inner member 2920 of the catheter 2915 relative to the outer member 2918. The locking mechanism 2935 can comprise, for example, a screw or some other type of locking mechanism that can be used to lock the position of the first piece 2928 of the handle 2925 relative to the second piece 2930.

With reference still to FIG. 8, a housing 2940 is located at or near a distal end of the catheter 2915. The housing 2940 is attached to a distal end of the outer member 2918 of the catheter 2915 but not attached to the inner member 2920. As described in more detail below, the housing 2940 defines an inner cavity that is sized to receive the flow control device 110 therein.

Figure 9:
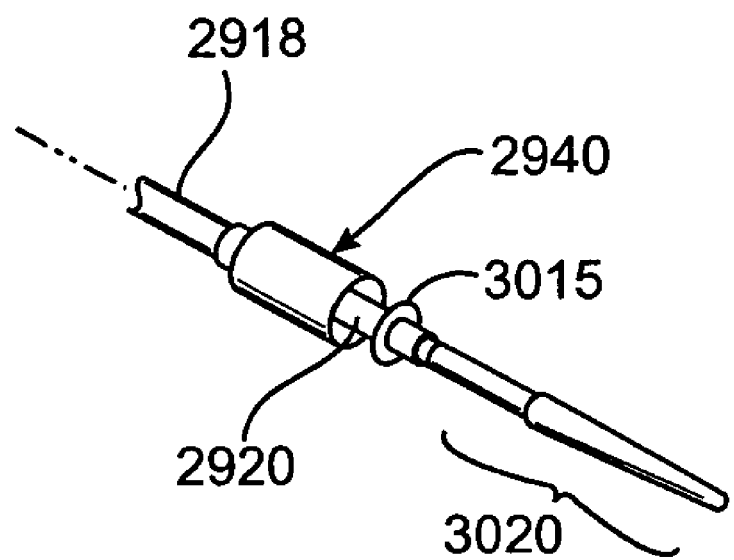
FIG. 9 shows a perspective view of a distal region of a delivery catheter of the delivery system.
Figure 10:
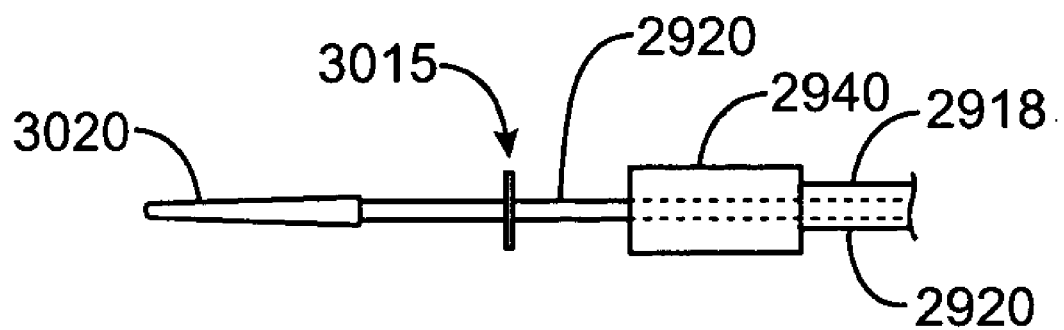
FIG. 10 shows a plan, side view of the distal region of the delivery catheter.

FIG. 9 shows an enlarged, perspective view of the portion of the distal portion of the catheter 2915 where the housing 2940 is located. FIG. 10 shows a plan, side view of the distal portion of the catheter 2915 where the housing 2940 is located. As shown in FIGS. 9 and 10, the housing 2940 is cylindrically-shaped and is open at a distal end and closed at a proximal end. The inner member 2920 of the catheter 2015 protrudes through the housing and can be slidably moved relative to the housing 2940. An ejection member, such as a flange 3015, is located at a distal end of the inner member 2920. As described below, the ejection member can be used to eject the flow control device 110 from the housing 2940. The flange 3015 is sized such that it can be received into the housing 2940. The housing can be manufactured of a rigid material, such as steel. The housing 2940 preferably has an interior dimension such that the flow control device 110 is in a compressed state when the flow control device 110 is positioned in the housing 2940.

In one embodiment, a tip region 3020 is located on the distal end of the inner member 2920, as shown in FIGS. 9 and 10. The tip region 3020 can be atraumatic in that it can have a rounded or cone-shaped tip that facilitates steering of the catheter 2915 to a desired bronchial passageway location. The atraumatic tip region 3020 preferably includes a soft material that facilitates movement of the atraumatic tip region 3020 through the trachea and bronchial passageway(s).

The inner member 2920 of the catheter 2915 can include a central guide wire lumen that extends through the entire length of the catheter 2915, including the atraumatic tip region 3020, if present. The central guide wire lumen of the inner member 2920 is sized to receive a guide wire, which can be used during deployment of the catheter 2915 to guide the catheter 2915 to a location in a bronchial passageway, as described more fully below.

As mentioned, the housing 2940 defines an interior cavity that is sized to receive the flow control device 110. This is described in more detail with reference to FIG. 11, which shows a cross-sectional view of the housing 2940 with a flow control device 110 positioned within the housing 2940. For clarity of illustration, the flow control device 110 is represented as a dashed box in FIG. 11. The housing 2940 can be sufficiently large to receive the entire flow control device 110 without any portion of the flow control device protruding from the housing 2940, as shown in FIG. 11.

Alternately, the housing 2940 can be sized to receive just a portion of the flow control device 110. For example, the distal end 604 of the flow control device 110 can be shaped to protrude out of the housing 2940 when the flow control device 110 is positioned within the housing 2940.

Figure 11:
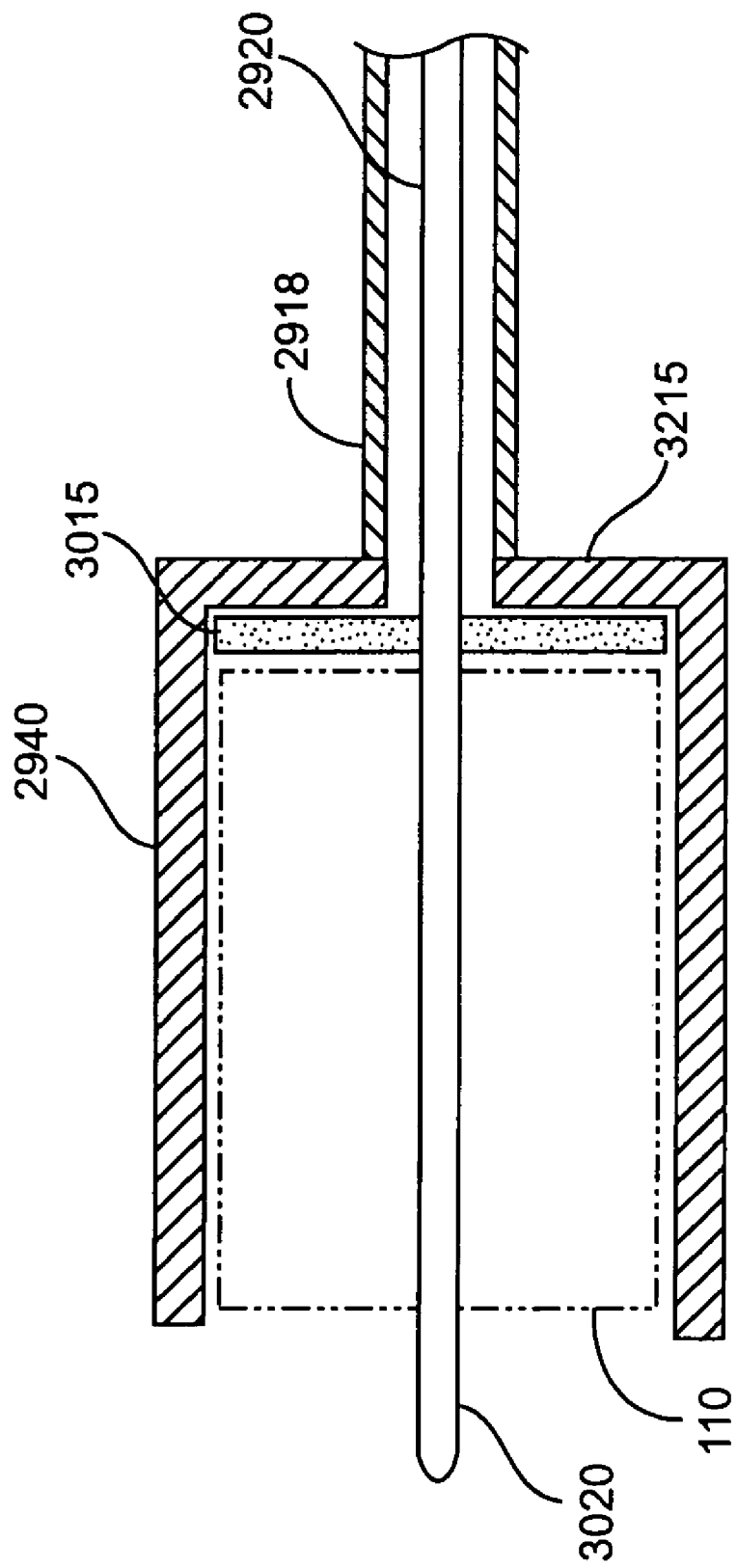
FIG. 11 shows a cross-sectional view of a housing of the delivery catheter, the housing containing a flow control device.

As shown in FIG. 11, the flow control device 110 abuts or is adjacent to the flange 3015 of the catheter inner member 2920 when the flow control device is positioned within the housing 2940. As mentioned, the catheter inner member 2920 is moveable relative to the housing 2940 and the catheter outer member 2918. In this regard, the flange 3015 can be positioned to abut a base portion 3215 of the housing 2940 so that the flange 3015 can act as a detent for the range of movement of the catheter inner member 2920 relative to the catheter outer member 2918.

As described in more detail below, the catheter 2915 can be used to deliver a flow control device 110 to a desired bronchial passageway location. This is accomplished by first loading the flow control device into the housing 2940 of the catheter 2915. The distal end of the catheter 2915 is then deployed to the desired bronchial passageway location such that the housing (and the loaded flow control device 110) are located at the desired bronchial passageway location. The flow control device 110 is then ejected from the housing 2940.

Loader System

Figure 12:
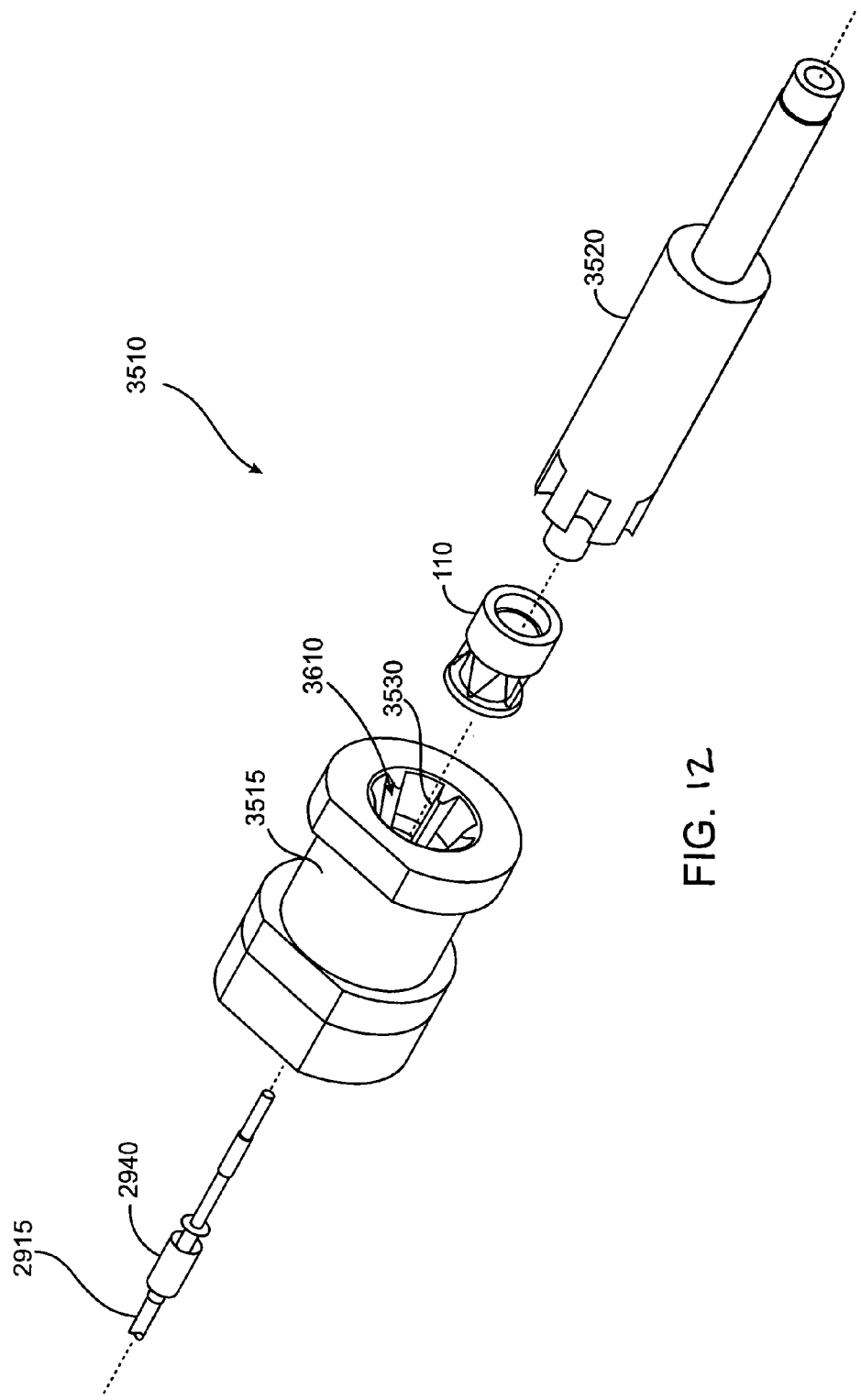
FIG. 12 is a perspective view of a loader system for loading the flow control device onto a delivery catheter.

As discussed above, the flow control device 110 is in a compressed state when it is mounted in the housing 2940 of the delivery catheter 2915. Thus, the flow control device 110 should be compressed to a smaller diameter prior to loading the flow control device 110 into the housing 2940 so that the flow control device 110 can fit in the housing. FIG. 12 shows a perspective view of one embodiment of a loader system 3510 for compressing the flow control device 110 to a smaller diameter and for inserting the flow control device 110 into the delivery catheter housing 2940. The loader system 3510 can be used to securely hold the catheter housing 2940 in place and to properly align the housing 2940 relative to the flow control device 110 during insertion of the flow control device 110 into the housing 2940. This facilitates a quick and easy loading of the flow control device 110 into the housing 2940 and reduces the likelihood of damaging the flow control device 110 during loading.

The loader system 3510 includes a loader device 3515 and a pusher device 3520. As described in detail below, the loader device 3515 is used to compress the flow control device 110 to a size that can fit into the housing 2940 and to properly align the flow control device 110 with the housing 2940 during insertion of the flow control device 110 into the housing 2940. The pusher device 3520 is configured to mate with the loader device 3515 during loading, as described more fully below. The pusher device 3520 is used to push the flow control device 110 into the loader device 3515 and into the housing 2940 during loading, as described in more detail below.

Figure 13:
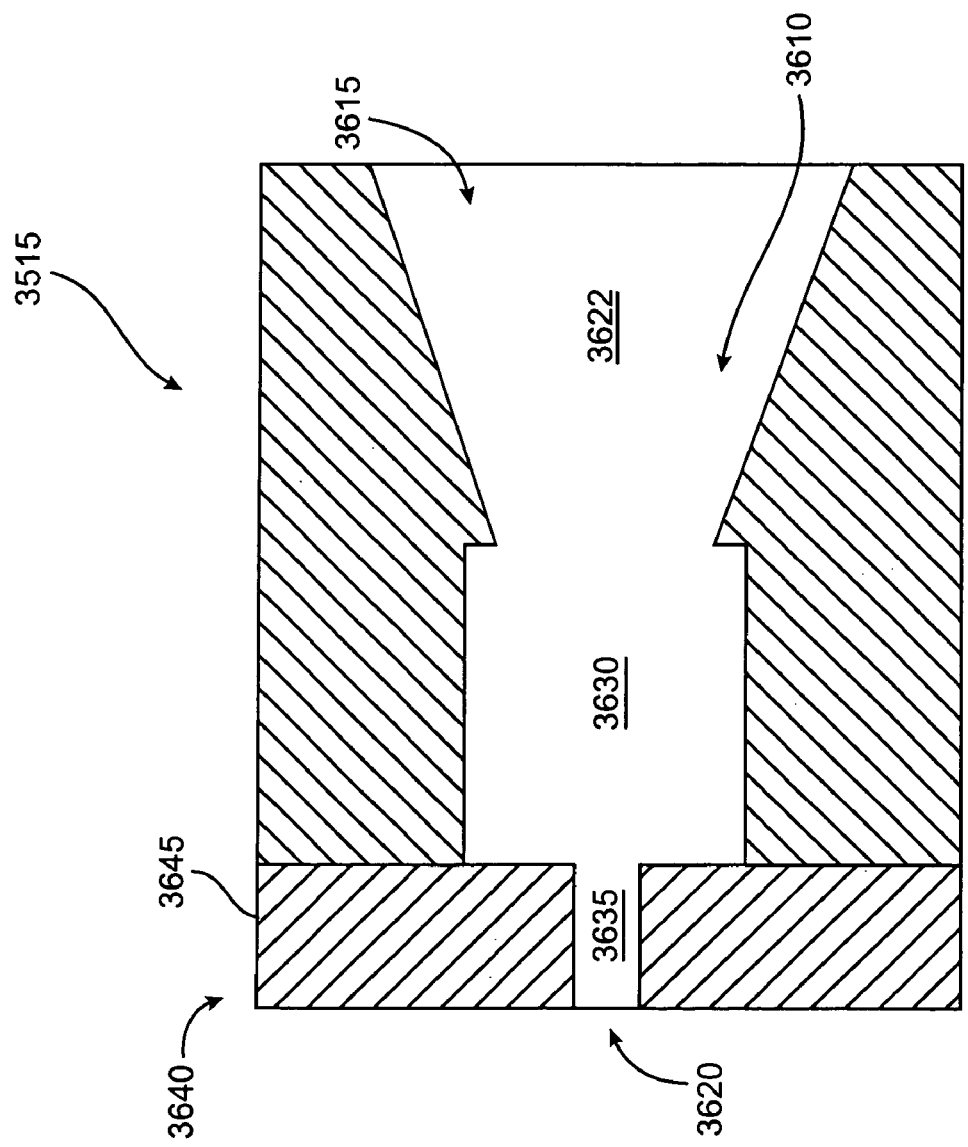
FIG. 13 shows a cross-sectional side view of a loader device of the loader system.

FIG. 13 is a schematic, cross-sectional view of one embodiment of the loader device 3515. A loading tunnel 3610 extends entirely through a main body of the loader device 3515 so as to form a front opening 3615 and an opposed rear opening 3620. The loading tunnel 3610 can have a circular cross-sectional shape, although it should be appreciated that the loading tunnel 3610 could have other cross-sectional shapes. The loading tunnel 3610 has three regions, including a funnel-shaped loading region 3622, a container or housing region 3630, and a catheter region 3635. The loading region 3622 of the loading tunnel 3610 gradually reduces in diameter moving in a rearward direction (from the front opening 3615 toward the rear opening 3620) so as to provide the loading region 3622 with a funnel shape. The housing region 3630 has a shape that substantially conforms to the outer shape of the catheter housing 2940 so that the catheter housing 2940 can be inserted into the housing region 3630, as described below. The catheter region 3635 is shaped to receive the outer member 2918 of the catheter 2915.

The loader device 3515 can also include a catheter locking mechanism 3640 comprised of a door 3645 that can be opened to provide the catheter 2915 with access to the housing region 3630 of the loading tunnel 3610. The door 3645 can be manipulated to vary the size of the rear opening 3620 to allow the housing 2940 to be inserted into the housing region 3630, as described in more detail below.

Figure 14:
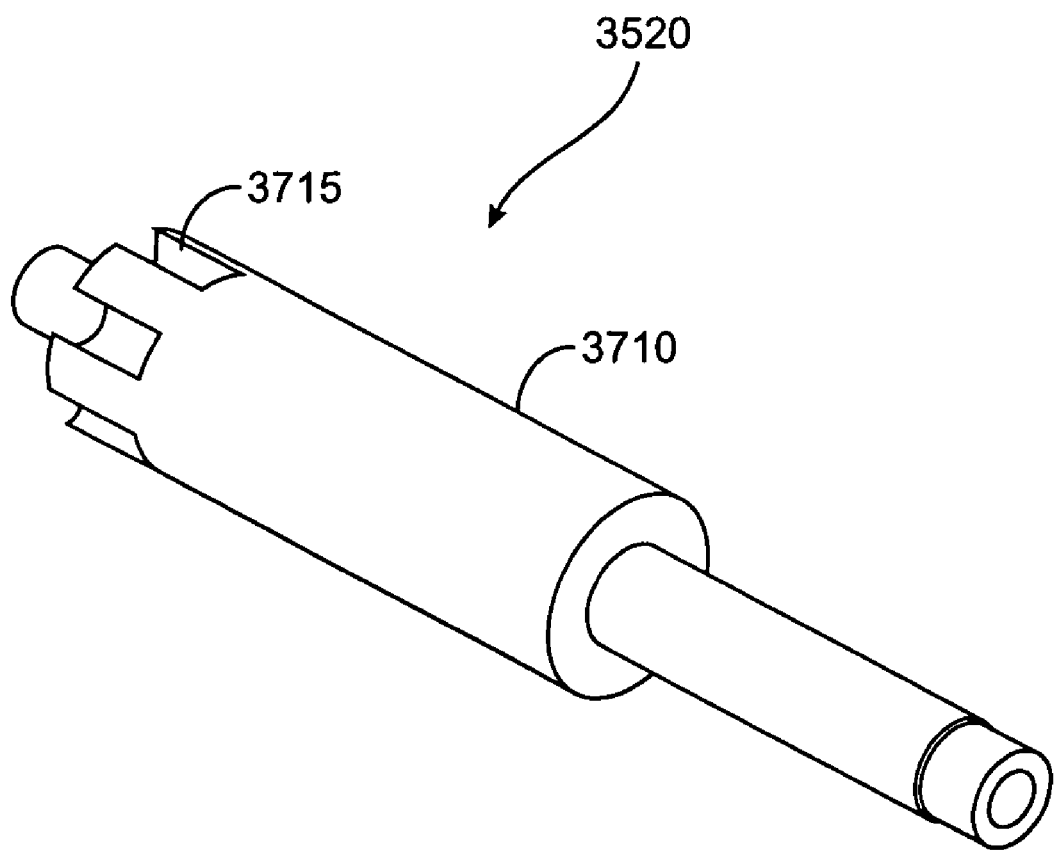
FIG. 14 shows a perspective view of a pusher device of the loader system.

FIG. 14 shows a perspective view of a first embodiment of the pusher device 3520. Additional embodiments of the pusher device 3520 are described below. The pusher device 3520 has an elongate shape and includes at least one piston 3710 that is sized to be axially-inserted into at least a portion of the loading region 3622 of the loader device loading tunnel 3610. The piston 3710 can have a cross-sectional shape that substantially conforms to the cross-sectional shape of the loading region 3622 in order to facilitate insertion of the piston 3710 into the loading region 3622. In one embodiment, the piston has one or more registration grooves 3715 that conform to the shape of corresponding registration grooves 3530 (shown in FIG. 12) in the loading tunnel 3610. When the grooves 3715, 3530 are used, the piston 3710 can be inserted into the loading tunnel 3610 of the loader device 3515 by aligning and mating the grooves to one another prior to insertion. The registration grooves 3715, 3530 can be used to ensure that the piston 3710 can only be inserted into the tunnel in a predetermined manner.

Figure 15:
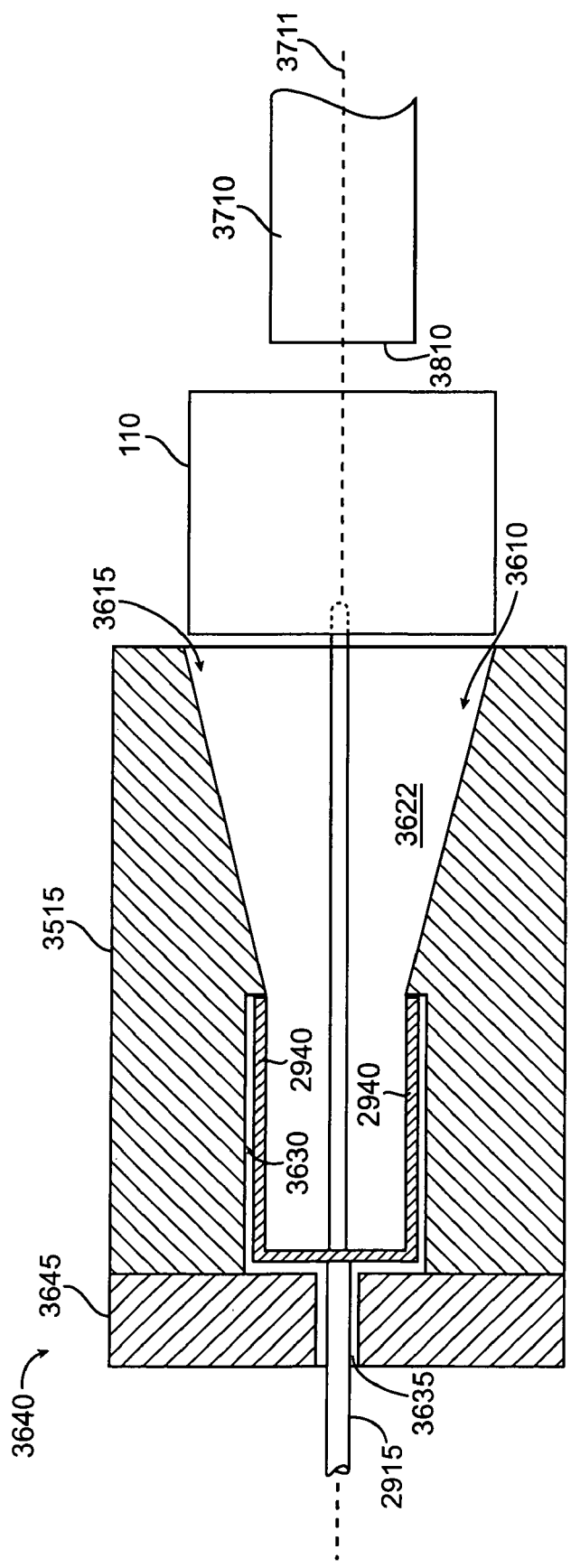
FIG. 15 shows the loader system readied for loading the flow control device into the housing of the delivery catheter.

With reference to FIGS. 15-18, the loader device 3515 is used in combination with the pusher device 3520 to compress the flow control device 110 and insert the flow control device 110 into the housing 2940 of the catheter 2915. As shown in FIG. 15, the delivery catheter 2915 is mated to the loader device 3515 such that the housing 2940 is positioned within the housing region 3630 of the loader device loading tunnel 3610 and the catheter 2915 is positioned within the catheter region 3635 of the loading tunnel 3610. When properly mated, the catheter housing 2940 is fixed in position relative to the loading region 3622 of the loading tunnel 3610. Furthermore, when the housing 2940 is positioned within the housing region 3630, the housing interior cavity is open to the loading region 3622 of the loader device 3515, such that the open end of the housing 2940 is registered with a rear edge of the loading region 3622.

With reference still to FIG. 15, after the catheter 2915 is mated with the loader device 3615, the flow control device 110 is positioned adjacent the front opening 3615 of the loading region 3622 of the loader device 3515. As shown in FIG. 15, the front opening 3615 is sufficiently large to receive the flow control device 110 therein without having to compress the size of the flow control device 110. Alternately, a slight compression of the flow control device 110 can be required to insert the flow control device 110 into the opening 3615. The pusher device 3520 is then positioned such that an end 3810 of the piston 3710 is located adjacent to the flow control device 110. The housing 2940, flow control device 110 and the piston 3710 are preferably all axially aligned to a common longitudinal axis 3711 prior to loading the flow control device 110 into the housing 2940. However, even if these components are not all axially aligned, the structure of the loader device 3515 will ensure that the components properly align during the loading process.

Figure 16:
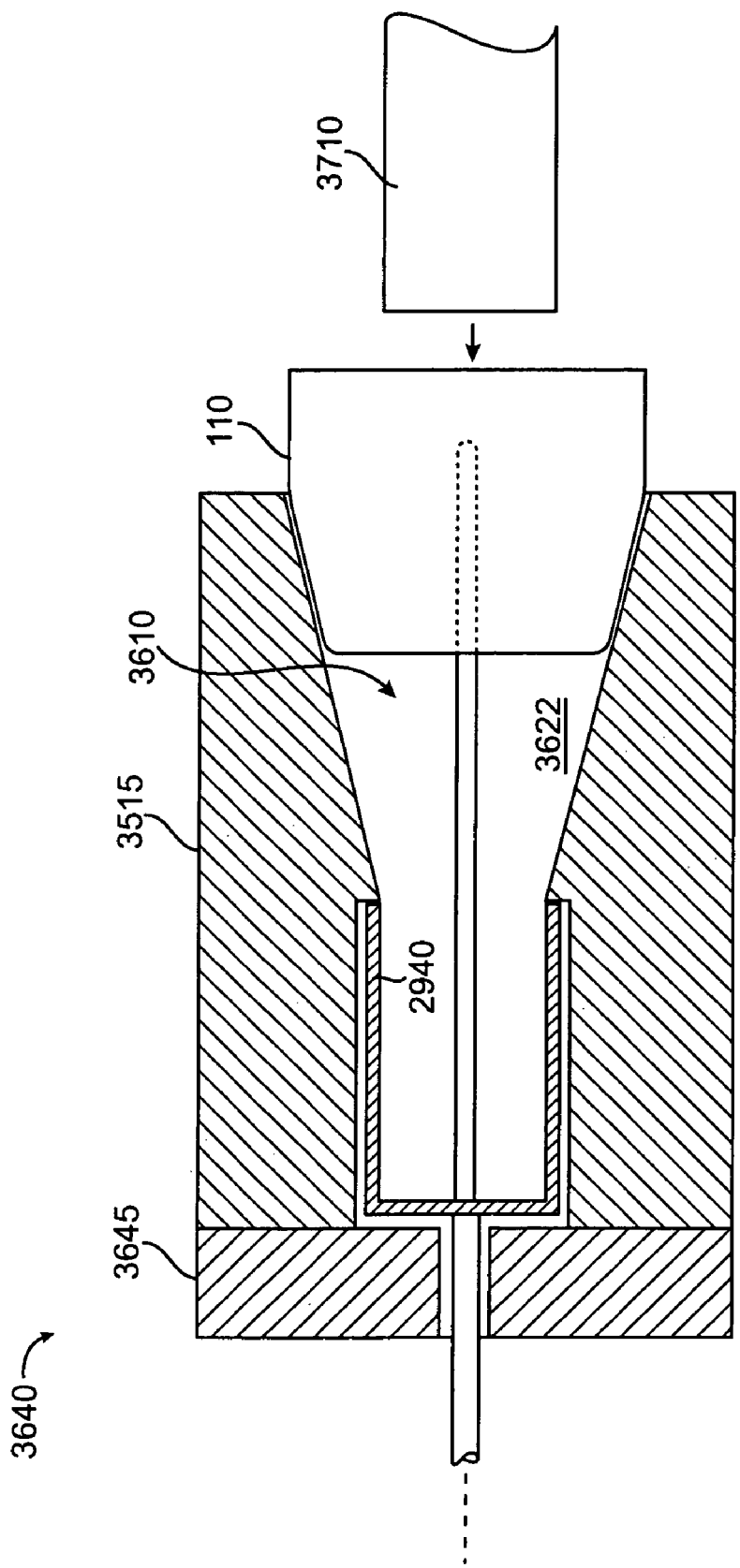
FIG. 16 shows the loader system being used to compress the flow control device during loading of the flow control device into the housing of the delivery catheter.

With reference now to FIG. 16, the piston 3710 of the pusher device 3520 is then used to push the flow control device into the loading region 3622 of the loading tunnel 3610 through the front opening 3615 in the tunnel. In this manner, the flow control device 110 moves through the loading tunnel 3610 toward the housing 2940. As this happens, the funnel-shape of the loading region 3622 will cause the flow control device 110 to be gradually compressed such that the diameter of the flow control device is gradually reduced as the flow control device 110 moves toward the housing 2940. The walls of the loading tunnel 3610 provide an equally balanced compressive force around the entire circumference of the flow control device 110 as the flow control device is pushed through the loading tunnel 3610. This reduces the likelihood of deforming the flow control device during compression.

Figure 17:
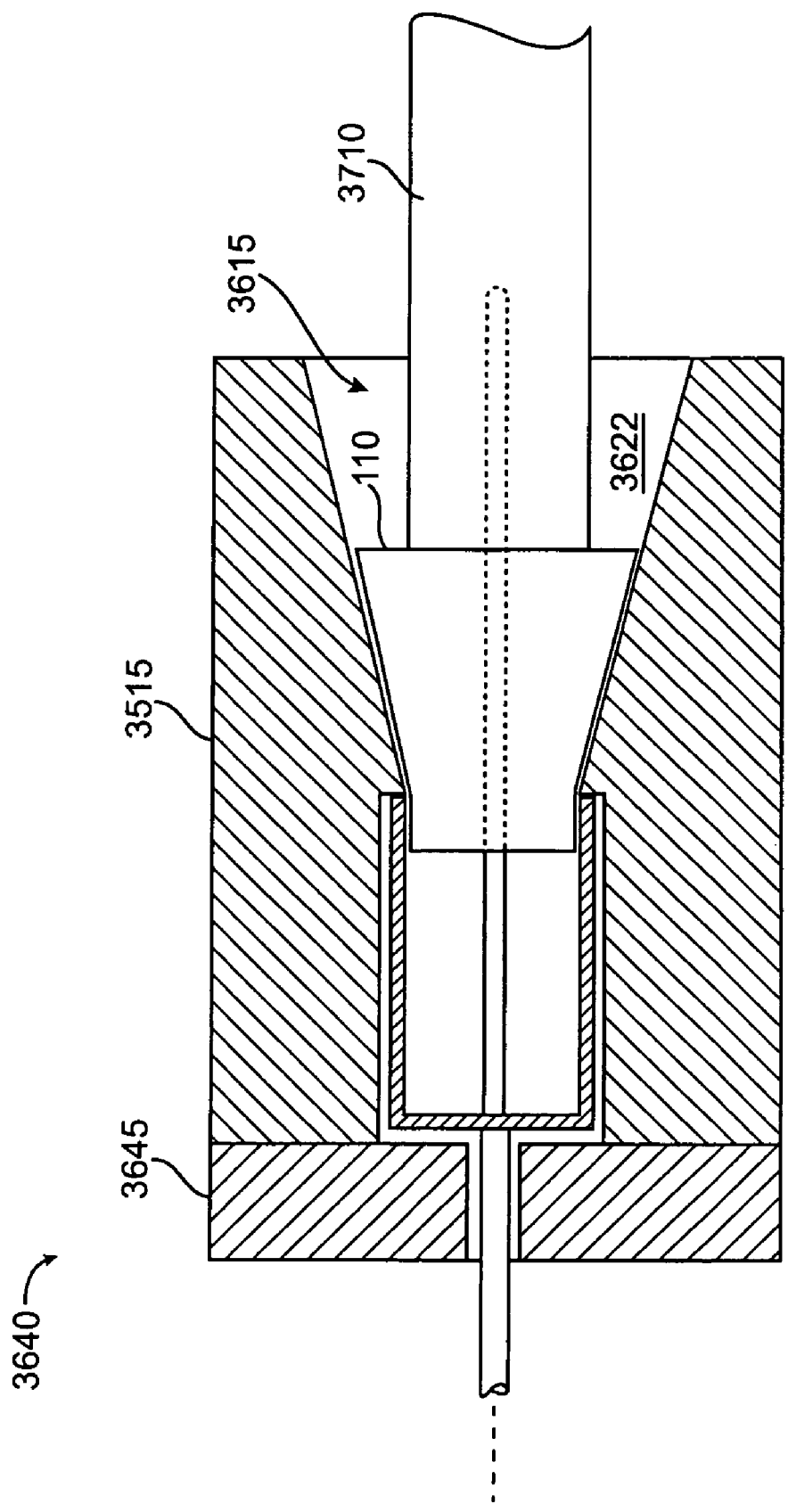
FIG. 17 shows the loader system being used to compress the flow control device during insertion of the flow control device into the housing of the delivery catheter.

As shown in FIG. 17, as the flow control device is pushed toward the housing 2940, the flow control device 110 will eventually be compressed to a size that permits the flow control device to be pushed into the housing 2940. In one embodiment, the loading region 3622 of the loading tunnel 3610 reduces to a size that is smaller than the opening of the housing 2940 so that the flow control device 110 can slide easily into the housing 2940 without any snags. Alternately, the opening in the housing 2940 can be substantially equal to the smallest size of the loading region 3625.

Figure 18:
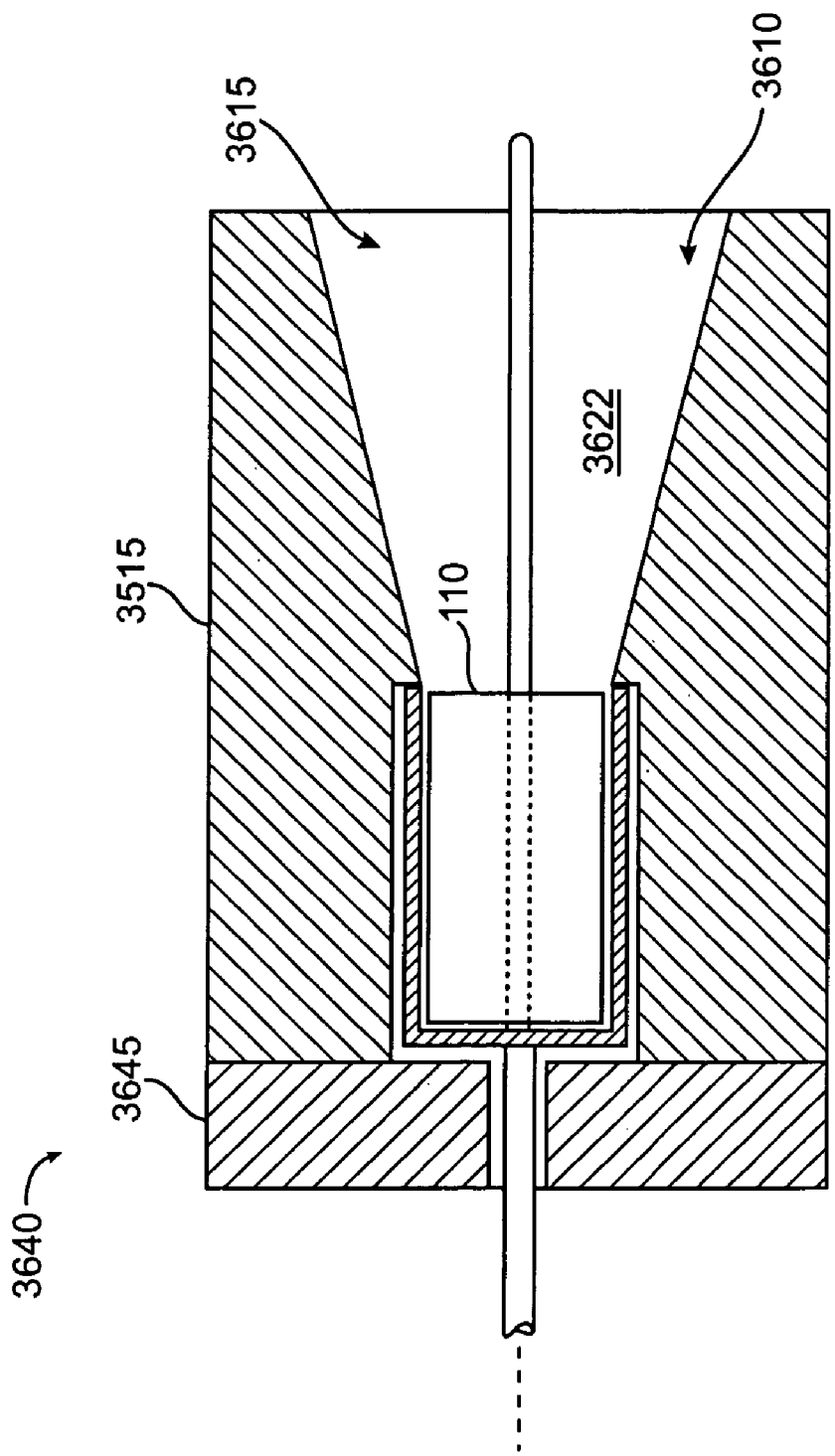
FIG. 18 shows the loader system with the flow control device fully loaded into the housing of the delivery catheter.
Figure 19:
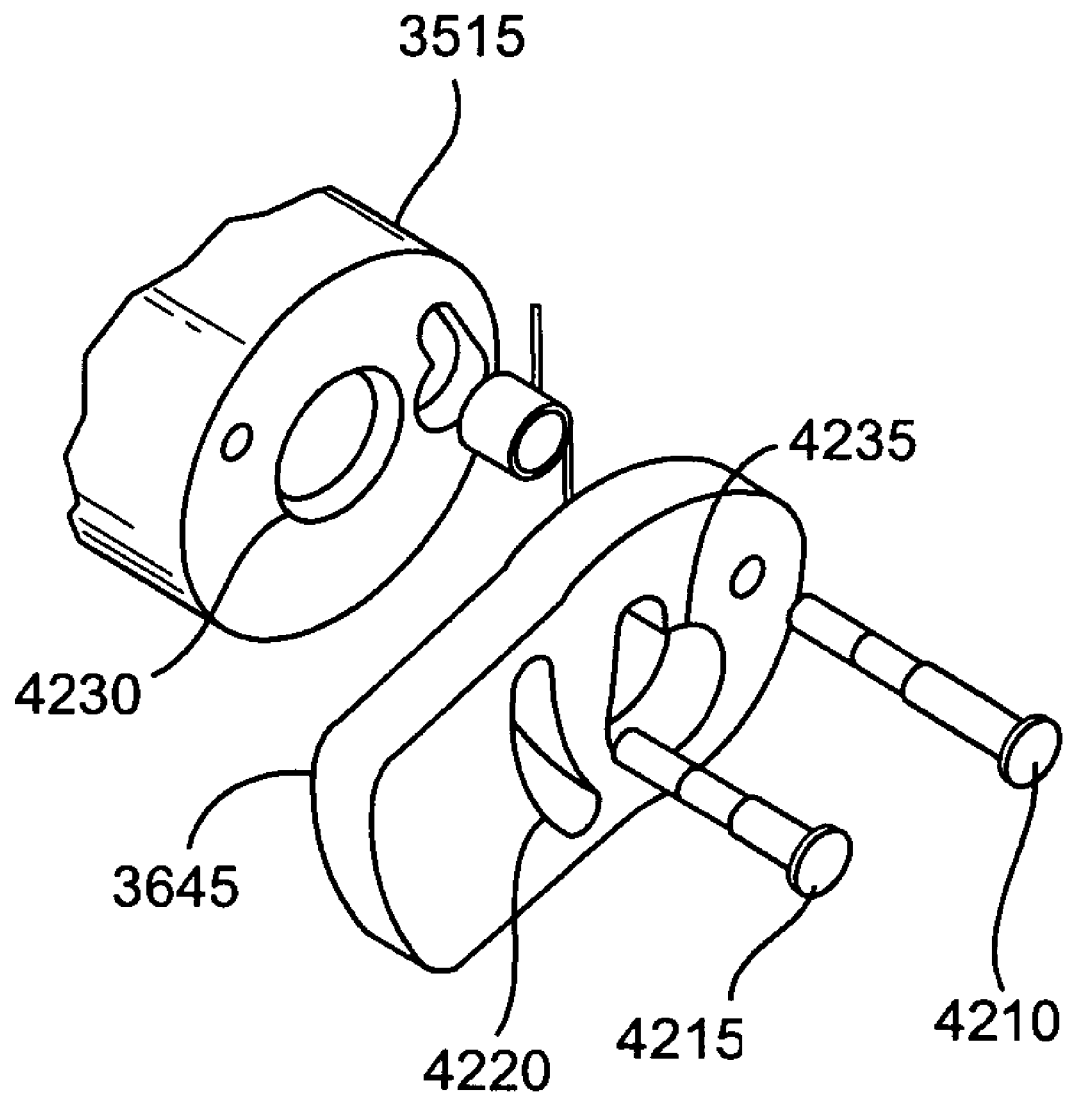
FIG. 19 shows an exploded, perspective rear view of the loader device of the loader system.

As shown in FIG. 18, the pusher device 3520 continues to push the flow control device 110 into the loader device 3515 until the entire flow control device 110 is located inside the housing 2940. The pusher device 3520 can then be removed from the loader device 3515. The catheter 2915 and the housing 2940 (which now contains the loaded flow control device 110) can then also be removed from the loader device 3515.

As mentioned above, an embodiment of the loader device 3515 includes a locking mechanism 3640 that is used to lock and position the catheter 2915 and catheter housing 2940 relative to loader device 3515 during loading of the flow control device 110 into the housing 2940. An exemplary locking mechanism 3640 is now described with reference to FIGS. 19-23, although it should be appreciated that other types of locking mechanisms and other locking procedures could be used to lock and position the catheter 2915 and catheter housing 2940 relative to loader device 3515 during loading.

As mentioned, the locking mechanism can comprise a door 3645 that can be moved to facilitate insertion of the catheter housing 2940 into the loader device 3515. Such a locking mechanism 3640 is described in more detail with reference to FIG. 19, which shows an exploded, rear, perspective view of the loading member 3515. The locking mechanism 3640 comprises a door 3645 that is pivotably-attached to a rear surface of the loader device 3515 by a first pin 4210. A second pin 4215 also attaches the door 3645 to the loader device 3515. The second pin extends through an arc-shaped opening 4220 in the door 3645 to provide a range of pivotable movement for the door 3645 relative to the loader device 3515, as described more fully below. The rear surface of the loader device 3515 has an opening 4230 that opens into the housing region 3630 of the loading tunnel 3610 in the loader device 3515. When mounted on the loader device 3515, the door 3645 can partially block the opening 4230 or can leave the opening unblocked, depending on the position of the door 3645. The door 3645 includes an irregular shaped entry port 4235 through which the catheter 2915 and catheter housing 2940 can be inserted into the opening 4230.

Figure 20:
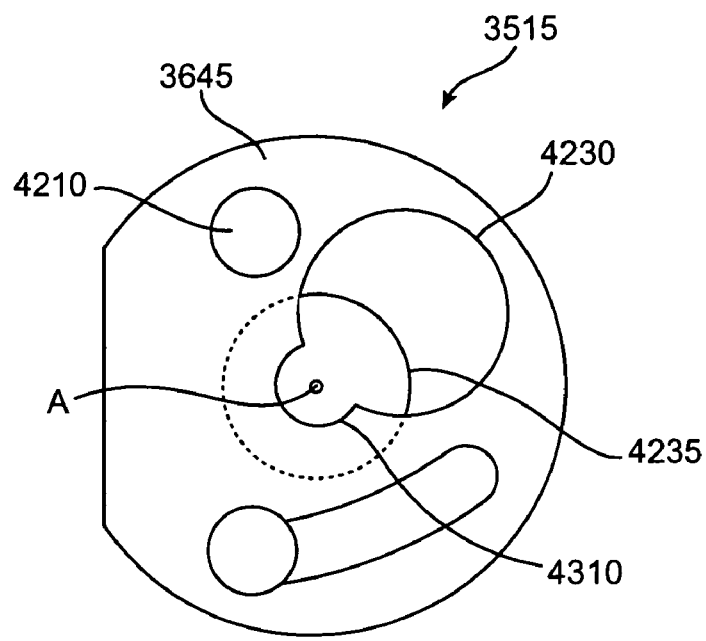
FIG. 20 shows a plan, rear view of the loader device of the loader system with a delivery door in a closed position.
Figure 21:
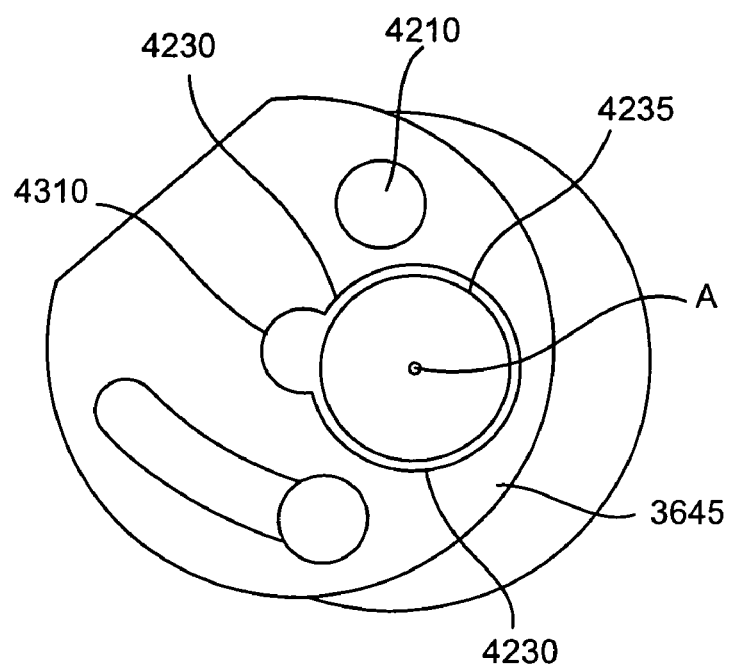
FIG. 21 shows a plan, rear view of the loader device of the loader system with a delivery door in an open position.
Figure 22:
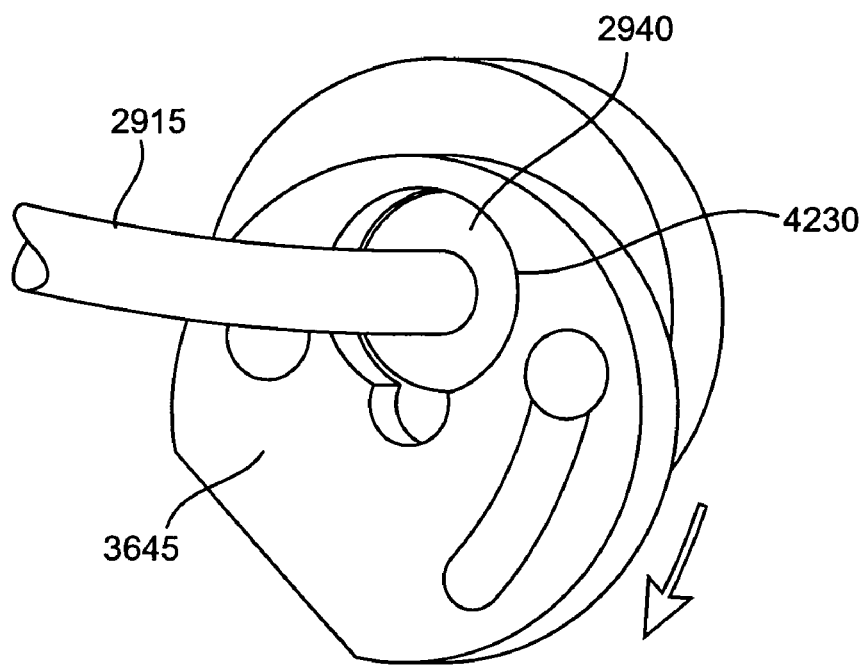
FIG. 22 shows a perspective, rear view of the loader device of the loader system with the delivery door in an open position and the catheter housing inserted into the loader device.
Figure 23:
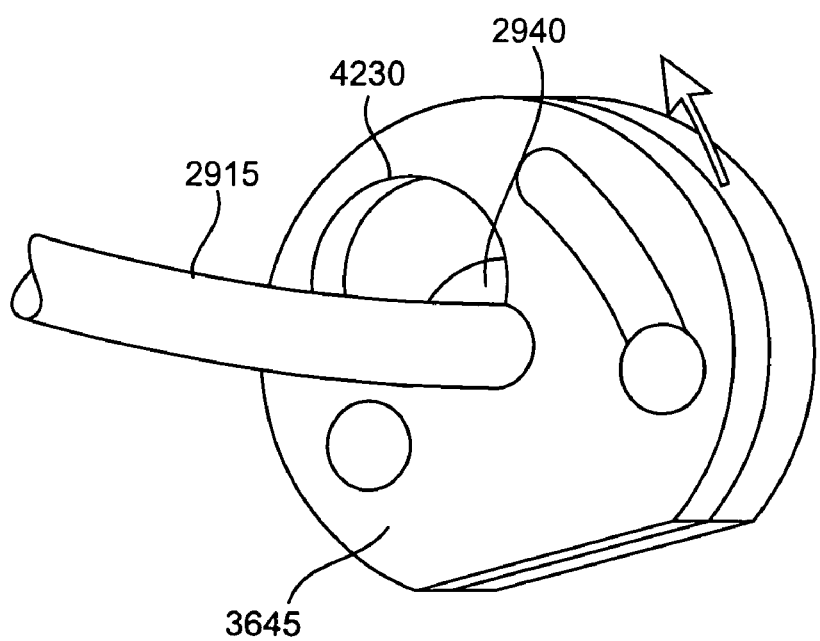
FIG. 23 shows a perspective, rear view of the loader device of the loader system with the delivery door in a closed position and the catheter housing mated with the loader device.

FIG. 20 shows a rear view of the loader device 3515 with the door 3645 in a default, closed state. When in the closed state, the door partially occludes the opening 4235. The entry port 4230 includes a catheter region 4310 that is sized to receive the outer member 2918 of the catheter 2915. The catheter region 4310 is aligned with a central axis A of the opening 4230 in the loader device 3515 when the door 3645 is closed. As shown in FIG. 21, the door 3645 can be moved to an open position by rotating the door 3645 about an axis defined by the first pin 4210. When the door is in the open position, the entry port 4230 is positioned such that a large portion of the entry port 4230 is aligned with the opening 4235 in the loader device 3515 so that the opening 4230 is unblocked. This allows the housing 2940 of the catheter 2915 to be inserted into the housing region 3630 through the aligned entry port 4230 and opening 4235 while the door 3645 is in the open position, as shown in FIG. 22. The door 3645 can then be released and returned to the closed position, such that the door 3645 partially blocks the opening 4230 and thereby retains the housing 2940 within the housing region 3630, as shown in FIG. 23. The door 3645 can be spring-loaded so that it is biased toward the closed position.

Methods of Use

Disclosed is a method of deploying a flow control device 110 to a bronchial passageway in order to regulate or eliminate airflow to or from a targeted lung region. The deployed flow control device 110 can eliminate air flow into the targeted lung region and result in collapse of the targeted lung region. However, the deployed flow control device 110 need not result in the collapse of the targeted lung region in order to gain a beneficial effect. Rather, the flow control device 110 can regulate airflow to and from the targeted lung region to achieve an improved air flow dynamic, such as by eliminating airflow into the targeted lung region during inhalation, but not resulting in collapse. The deployment of the flow control device 110 can channel or redirect the inhaled air to a non-isolated, healthier region of the lung, thus improving ventilation to the healthier lung tissue, and improving ventilation-perfusion matching in the healthier lung region. The exhaled air of the targeted lung region can still be vented through the implanted one-way flow control device 110, and thus the exhalation dynamics of the targeted lung region need not be affected by the presence of the flow control device. This can result in an increase in the efficiency of oxygen uptake in the lungs.

The method of deployment and treatment can be summarized according to the following steps. It should be appreciated that some of the steps are optional and that the steps are not necessarily performed in the order listed below. The steps include:

(a) identifying a targeted lung region and determining a target location in bronchial passageway(s) to which the flow control device will be deployed (b) determining the diameter of the target location in the bronchial passageway(s) and selecting an appropriately sized flow control device for deploying in the lumen of the bronchial passageway; as described below, this step is optional, as a flow control device can be manufactured to span a wide range of bronchial diameters so that lumen measurement would not be necessary;

(c) loading the selected flow control device into a delivery device, such as the delivery catheter described above, for delivering and deploying the flow control device to the bronchial passageway; this step is optional, as the flow control device can be manufactured or obtained pre-loaded in a delivery device;

(d) positioning the delivery catheter within the bronchial passageway so that the flow control device is positioned at the target location in the bronchial passageway;

(e) deploying the flow control device at the target location in the bronchial passageway;

(f) removing the delivery device;

(g) performing one or more procedures on the targeted lung region and/or allowing reactions to occur in the targeted lung region as a result of the presence of the flow control device.

According to step (a), a physician or technician evaluates the diseased area of a patient's lung to determine the targeted lung region and then determines the bronchial passageway(s) that provide airflow to the targeted lung region. Based on this, one or more target locations of bronchial passageways can be determined to which one or more flow control devices can be deployed.

In step (b), the proper size of a flow control device for insertion into the bronchial passageway is determined. As mentioned, this step is optional, as a flow control device can be manufactured to span a wide range of bronchial diameters so that lumen measurement would not be necessary. It should be appreciated that a precise match between the size of the flow control device 110 and the lumen of the bronchial passageway is not required, as the compressibility and expandability of the flow control device 110 provides a variation in size. In one embodiment, the flow control device is selected so that its size is slightly larger than the size of the bronchial passageway.

In step (c), the flow control device is loaded onto a delivery system, such as the delivery system 2910 comprised of the catheter 2915 that was described above with reference to FIG. 31. If the delivery system 2910 is used, the flow control device 110 is loaded into the housing 2940 at the distal end of the catheter 2915, such as by using any of the loader systems described herein. Alternately, the flow control device 110 can be loaded into the housing 2940 by hand. As mentioned, the loading step can be optional, as the flow control device 110 can be manufactured or obtained with the flow control device pre-loaded. It should be appreciated that other delivery systems could also be used to deliver the flow control device to the bronchial passageway.

Figure 24:
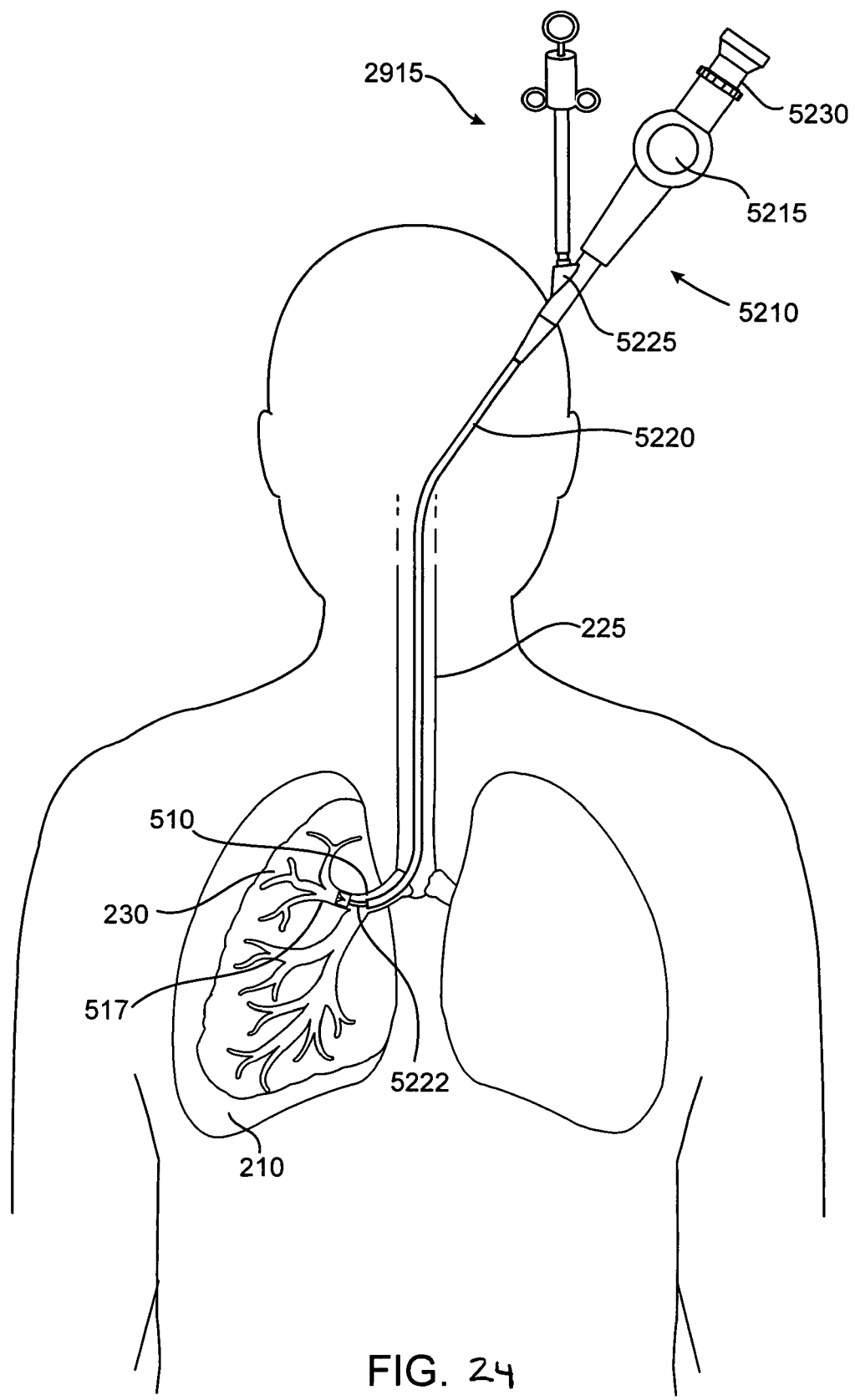
FIG. 24 shows a bronchoscope deployed within a bronchial tree of a patient.

In step (d), the delivery catheter is inserted into the bronchial passageway so that the flow control device 110 is positioned at a desired location in the bronchial passageway. This can be accomplished by inserting the distal end of the delivery catheter 2915 into the patient's mouth or nose, through the trachea, and down to the target location in the bronchial passageway. The delivery of the delivery catheter 2915 to the bronchial passageway can be accomplished in a variety of manners. In one embodiment, a bronchoscope is used to deliver the delivery catheter 2915. For example, with reference to FIG. 24, the delivery catheter 2915 can be deployed using a bronchoscope 5210, which in an exemplary embodiment has a steering mechanism 5215, a shaft 5220, a working channel entry port 5225, and a visualization eyepiece 5230. The bronchoscope 5210 has been passed into a patient's trachea 225 and guided into the right primary bronchus 510 according to well-known methods.

Alternate Loader System

Figure 25A:
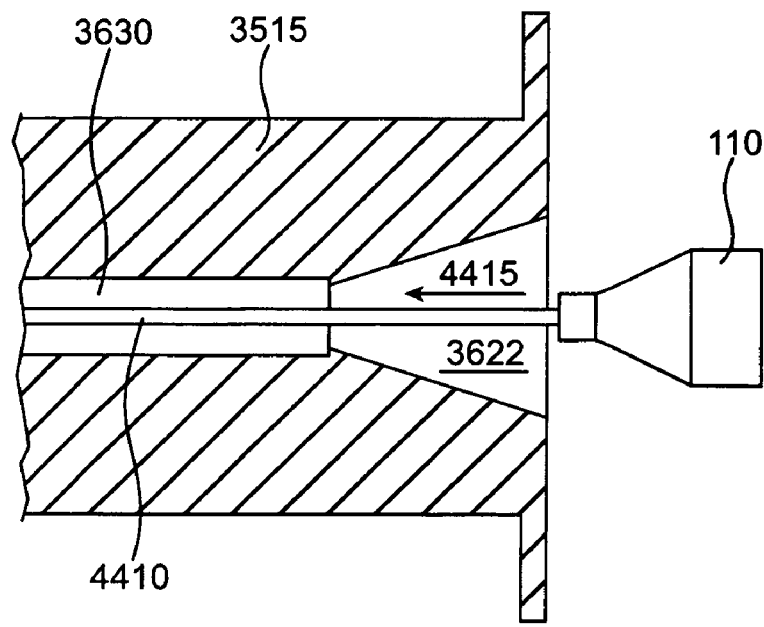
FIG. 25A shows an alternate embodiment of a loader system.

FIG. 25A shows another embodiment of a loader device 3515 that is configured to load the flow control device 110. The loader device 3515 includes a funnel-shaped loading region 3622 and a housing region 3630. As discussed, the loading region 3622 has a gradually-reducing diameter such that the flow control device 110 gradually reduces in diameter as the flow control device 110 is advanced through the loading region 3622. The housing region 3630 is sized to receive a container into which the flow control device 110 is loaded. In FIGS. 25A-32, for clarity of illustration, the flow control device 110 is sometimes represented schematically without showing structural details, although it should be appreciated that the flow control device has structural details not shown in the figures and is not limited to the schematic shape shown in the figures.

The container into which the flow control device 110 is loaded can be the catheter housing 2940 located on the distal end of the delivery catheter 2915, as described above. Alternately, the container can be a storage container into which the flow control device 110 is temporarily stored prior to being moved into the catheter housing 2940. For example, the storage container can comprise a tubular member that is sized to receive and retain the flow control device 110 in the compressed state. After the flow control device 110 is loaded into the storage container, an operator can transfer the flow control device from the storage container into the catheter housing 2940.

In an alternative embodiment, the loader device 3515 does not include a housing region 3630. In the alternative embodiment, the structure into which the flow control device 110 is loaded (e.g., the catheter housing 2940 or the storage container) is simply placed adjacent the loading region 3622 and positioned for receiving the flow control device in the compressed state. The loader device 3515 can include a structure that is configured to retain the catheter housing 2940 or the storage container in a position to receive the compressed flow control device from the loader device 3515.

As discussed, the flow control device 110 can be pushed through the loading region 3622, such as by using the pusher 3520. Alternately, the flow control device 110 can be pulled through the loading region 3622. For example, with reference to FIG. 25A, a puller or a pulling structure 4410 is attached to the flow control device. The pulling structure 4410 extends through the loading region 3622 of the loader device 3515 and extends outwardly from the loader device 3515. The pulling structure 4410 is pulled in the direction 4415 to thereby pull the flow control device 110 through the loading region 3622 so that the flow control device 110 is gradually compressed into the compressed state.

Figure 25B:
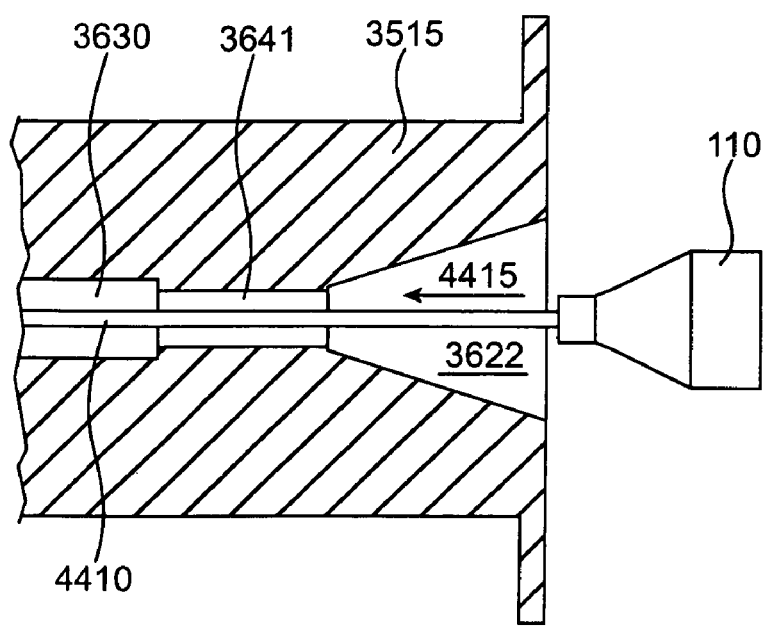
FIG. 25B shows another alternate embodiment of a loader system.

In an alternative embodiment shown in FIG. 25B, the flow control device 110 is transferred into the loader device 3515 in a first step, and then is transferred into the catheter housing 2940 in a second step. The loader device 3515 includes at least three regions: the loading region 3622, a transfer region 3641, and the housing region 3630. The loading region 3622 and the housing region 3630 are as described previously, and the transfer region 3641 is a tubular opening or cavity that is sized to receive and retain the flow control device 110 in the compressed state.

In a first step, a pulling structure 4410 is attached to the flow control device 110. The pulling structure 4410 may be a rigid structure, or may be a flexible structure such as suture or wire. As described above, the pulling structure 4410 extends through the loading region 3622 of the loader device 3515 and extends outwardly from the loader device 3515. The pulling structure 4410 is then pulled in the direction 4415 to thereby pull the flow control device 110 through the loading region 3622 and into the transfer region 3641 so that the flow control device 110 is gradually compressed into the compressed state.

Once the flow control device 110 is fully contained in the transfer region 3641, the pulling structure 4410 may then be removed or otherwise detached from the flow control device 110. In one embodiment of the pulling structure, the pulling structure 4410 is comprised of one or more flexible elements, such as suture or other flexible material, that are looped through a portion of the flow control device 110. Removing the pulling structure 4410 may include releasing one or more ends of the pulling structure. If the pulling structure is a suture, then removing the pulling structure can include cutting the suture. Once the pulling structure 4410 is removed, the distal end of the catheter housing 2940 is inserted into the housing region 3630. The compressed flow control device 110 may then be transferred into the catheter housing 2940 by pushing it through the transfer region 3641 and into the catheter housing, such as by using the pusher 3520.

Figure 26:
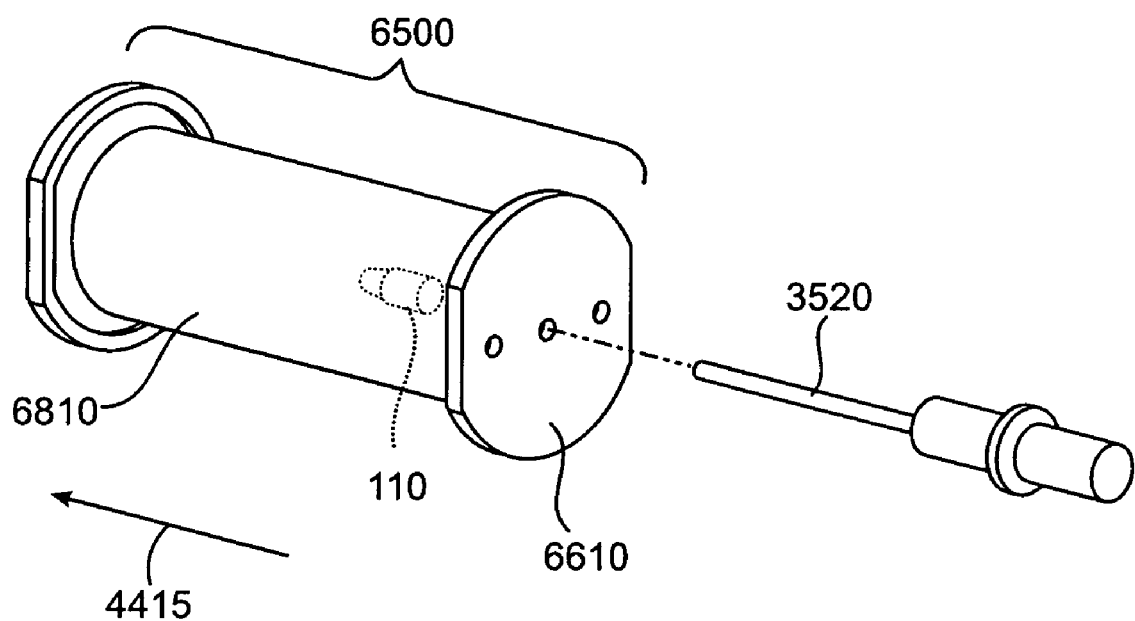
FIG. 26 shows a perspective view alternate embodiment of a loader system.

FIG. 26 shows another embodiment of a loader system that is similar to the previous embodiment shown in FIG. 25B. The loading system includes a loader assembly 6500 and a pusher 3520 that is used to push a flow control device 110 contained within the loader assembly 6500. The loader assembly 6500 includes a funnel assembly 6610 and a suture puller assembly 6810 that couples to the funnel assembly 6610, as described in detail below.

The funnel assembly 6610 includes a funnel housing 6620 (described below) that contains a loading region 3622, a transfer region 3641, and a housing region 3630 in a manner similar to the embodiment shown in FIG. 25B. The flow control device 110 is held inside the loading region 3622 of the funnel assembly 6610 by a pulling structure comprised of suture loops 6730 (shown in FIG. 28), which are threaded through a portion of the flow control device 110, as described more fully below.

Figure 27:
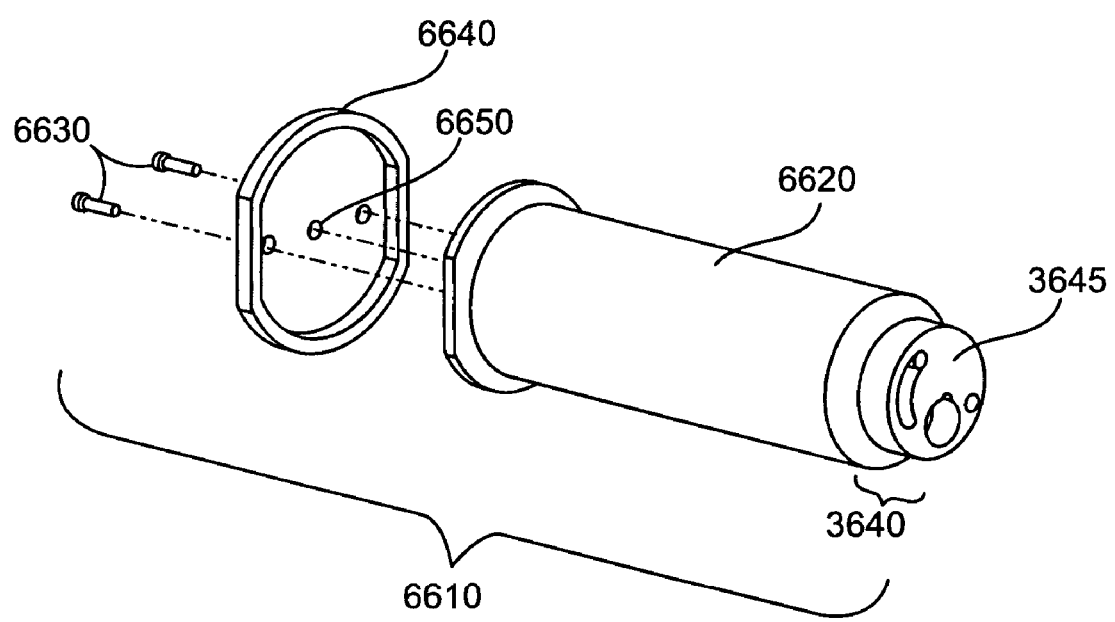
FIG. 27 shows an exploded, perspective view of a funnel assembly of the loader system of FIG. 26.

FIG. 27 shows an exploded, perspective view of the funnel assembly 6610, which includes the funnel housing 6620, a locking mechanism 3640, a funnel end cap 6640, and one or more end cap attachment screws 6630 that are used to attach the funnel end cap 6640 to the funnel housing 6620. The funnel housing 6620 is shown having a outer cylindrical shape with a flange-like base that mates with the funnel end cap 6640. However, it should be appreciated that the shape of the funnel housing 6620 can vary. The funnel housing 6620 is configured to be slidably coupled with the suture puller assembly 6810. The funnel housing 6620 has an outer dimension that is sized to be slidably received within a corresponding housing on the suture puller assembly 6810.

With reference still to FIG. 27, the locking mechanism 3640 includes a door 3645 that is movably attached to the funnel housing 6620 at the end opposite the funnel end cap 6640. As in the previous embodiment, the locking mechanism 3640 is used to lock and position the catheter 2915 and catheter housing 2940 relative to the funnel assembly 6610 during loading of the flow control device 110 into the housing 2940. An appropriate exemplary locking mechanism 3640 was described previously with reference to FIGS. 19-23, although it should be appreciated that other types of locking mechanisms and other locking procedures could be used to lock and position the catheter 2915 and catheter housing 2940 relative to the funnel assembly 6610 during loading.

Figure 32:
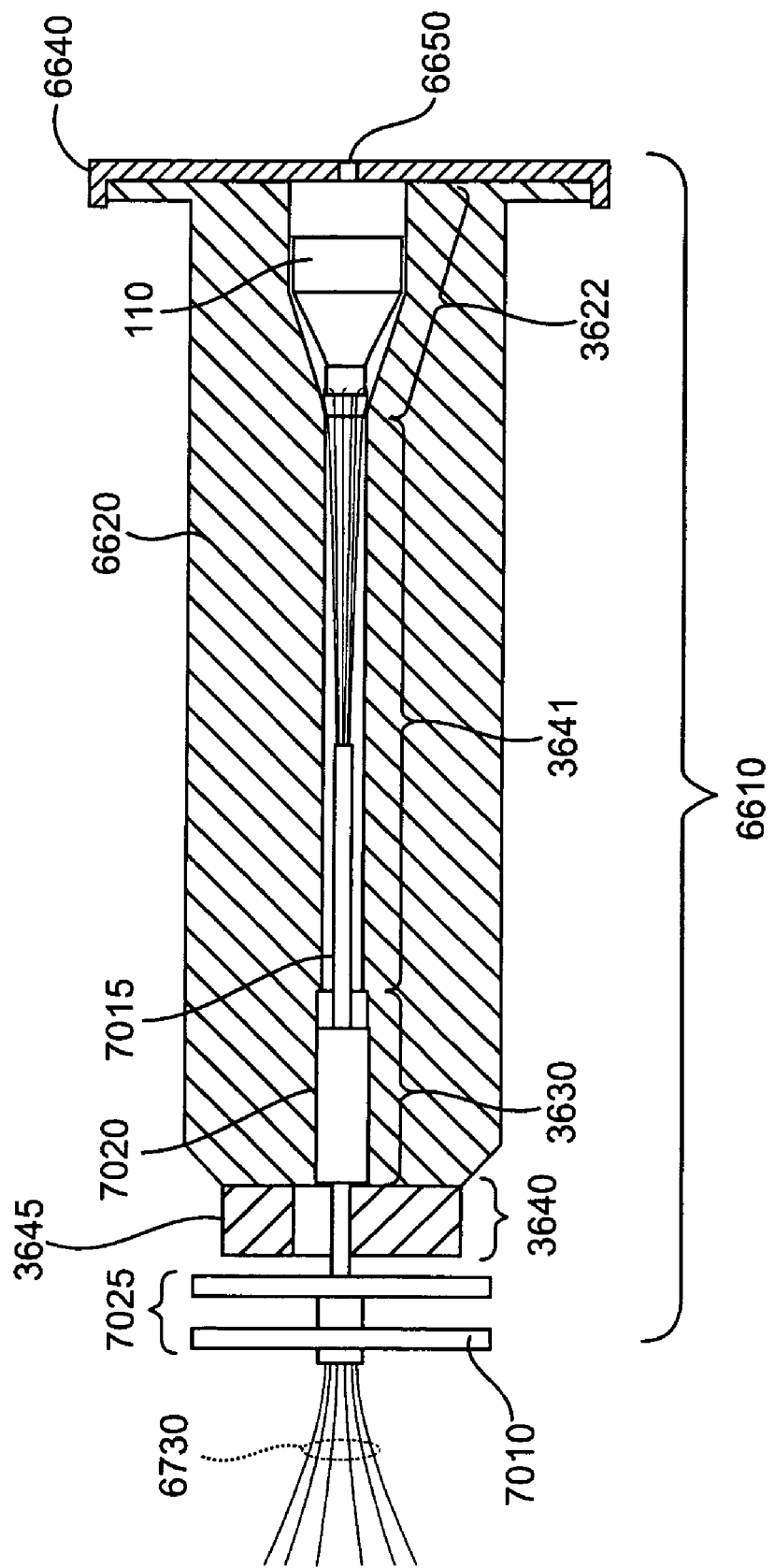
FIG. 32 shows a side, cross-sectional view of the funnel assembly with the flow control device positioned therein.

FIG. 32 shows a side-cross-sectional view of the funnel assembly 6610 with the flow control device 110 positioned within the loading region 3622. The funnel end cap 6640 encloses one end of the funnel housing 6620 to secure the flow control device therein. When the funnel end cap 6640 is unattached from the funnel housing 6620, the loading region 3622 is exposed to permit the flow control device 110 to be inserted within the loading region 3622. The loading region 3622 is of sufficient size to receive the flow control device 110 when the flow control device 110 is in the expanded state. As discussed above, the loading region 3622 is funnel shaped such that the flow control device can be radially compressed when pulled through the loading region 3622. Once the flow control device 110 has been threaded with the suture loops 6730 (as described below) and loaded into the loading region 3622 of the funnel housing 6620, the funnel end cap 6640 is attached to the funnel housing 6620 and secured thereto with the one or more end cap attachment screws 6630.

The end cap 6640 serves to protect and prevent inadvertent damage to the flow control device 110 while the flow control device 110 is positioned in the loading region 3622. With reference to FIGS. 27 and 32, the center of the funnel end cap 6640 has a guide hole 6650 that serves to guide the pusher 3520 (shown in FIG. 26) when the flow control device 110 is pushed into the catheter housing 2940 using the pusher 3520.

As discussed above, the flow control device 110 is held inside the loading region 3622 of the funnel assembly 6610 by a pulling structure comprised of suture loops 6730, which are threaded through a portion of the flow control device 110. The suture loops 6730 attach to at least a portion of the flow control device 110 for pulling of the flow control device 110 through the loader assembly 6500.

Figure 28:
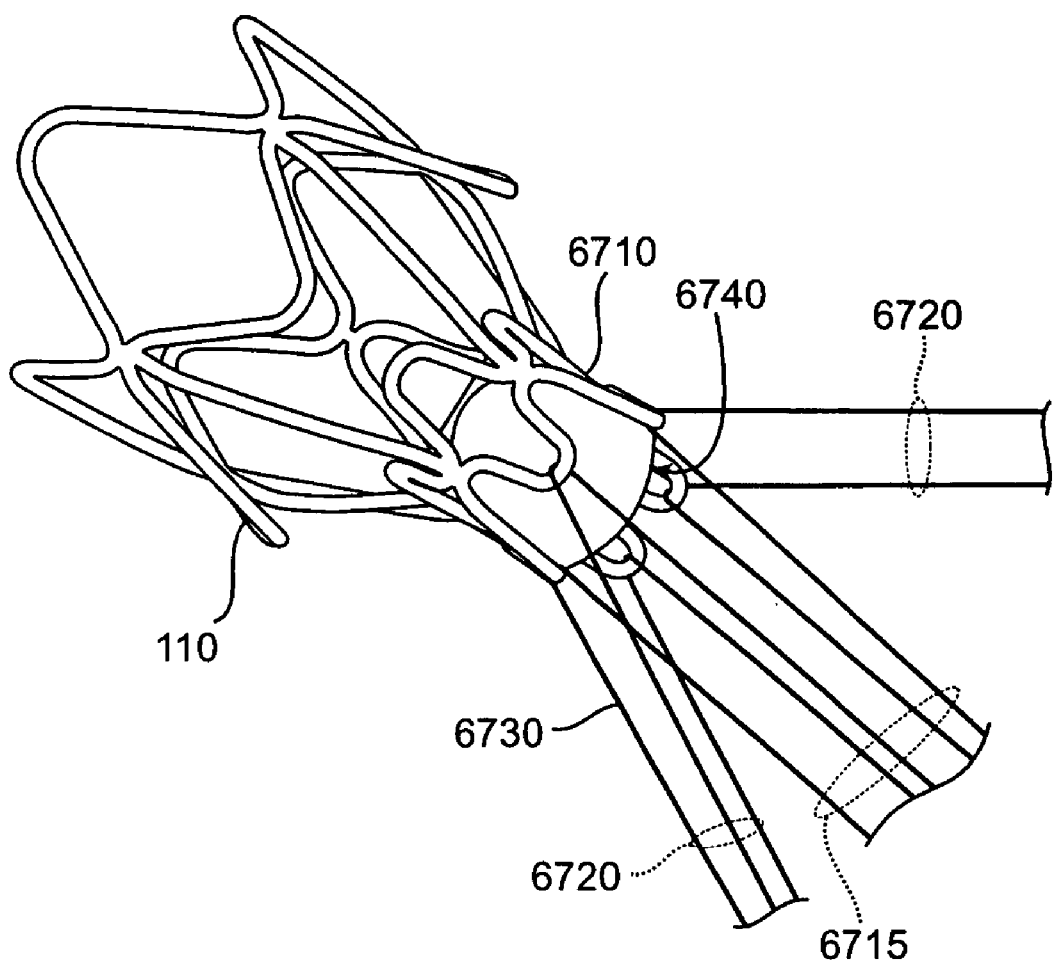
FIG. 28 shows an exemplary configuration of a flow control device attached to pulling structures comprised of sutures.

FIG. 28 shows an exemplary configuration of the flow control device 110 attached to sutures. In this embodiment, there are five loops of polypropylene monofilament suture threaded through a proximal end 6710 of the flow control device 110. However, there can be as few as one suture loop or more than five suture loops. Each suture loop has an inside strand 6715 and an outside strand 6720. The inside strand 6715 is the portion that is inside the inner diameter of the proximal end 6710 of the flow control device 110. The outside strand 6720 is the portion of the suture loop 6730 that is on the outside of the proximal end 6710 of the flow control device 110. The suture loops 6730 can be manufactured of any flexible material such as polyethylene, wire, silk or other material.

The flow control device 110 is attached to the suture loops in the manner shown in FIG. 28. When the flow control device 110 and attached suture loops 6730 are positioned in the funnel assembly 6610, the ends of the suture loops 6730 are threaded through the center of the funnel housing 6620 and through the loading region 3622, the transfer region 3641, the housing region 3630, and finally through the center opening in the door 3645 of the locking mechanism 3640, as shown in FIG. 32. The suture loop ends are then attached to the suture puller assembly 6810, as described in more detail below.

Figure 29:
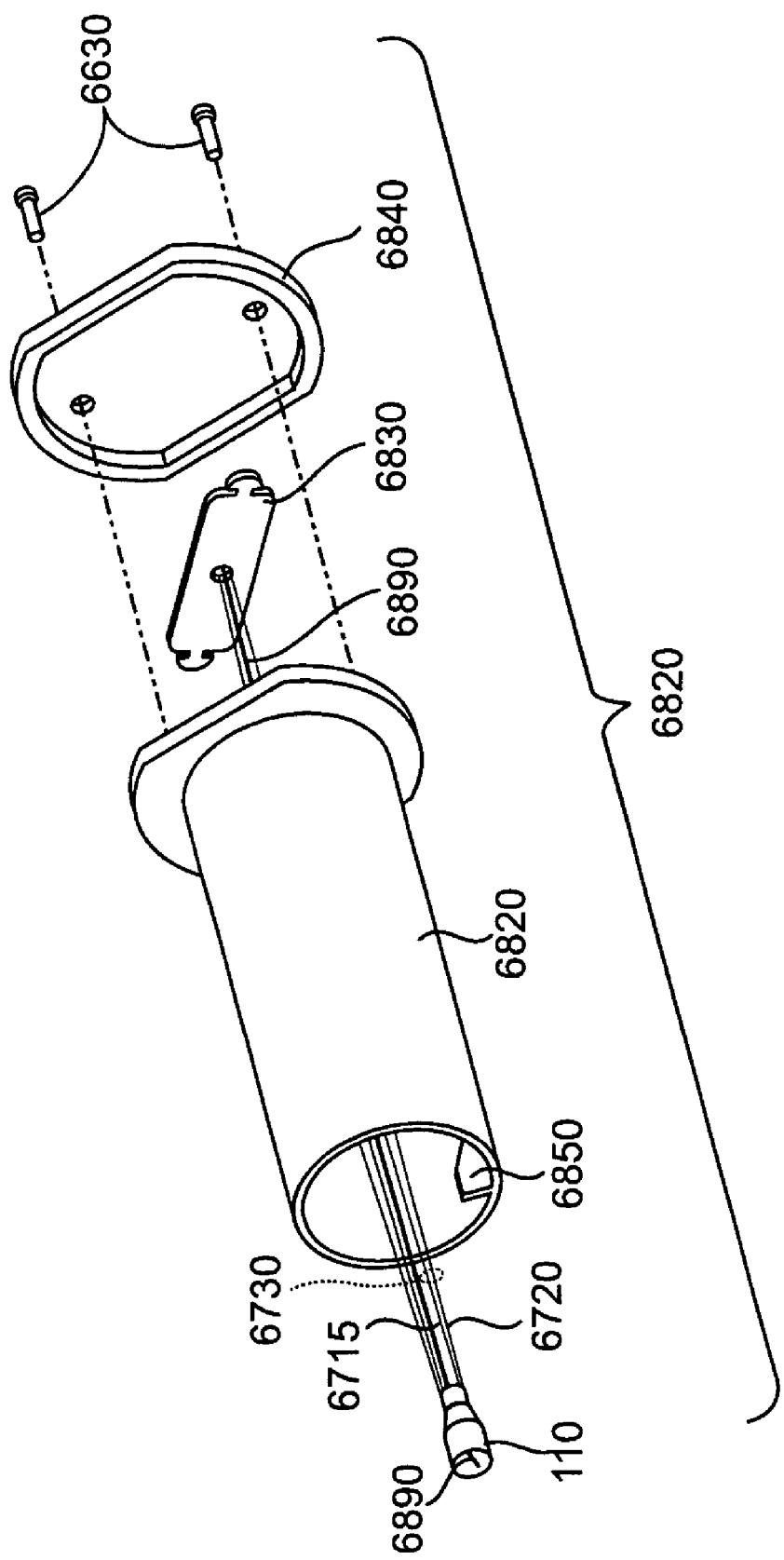
FIG. 29 shows an exploded view of a suture puller assembly of the loader system of FIG. 26.
Figure 3O:
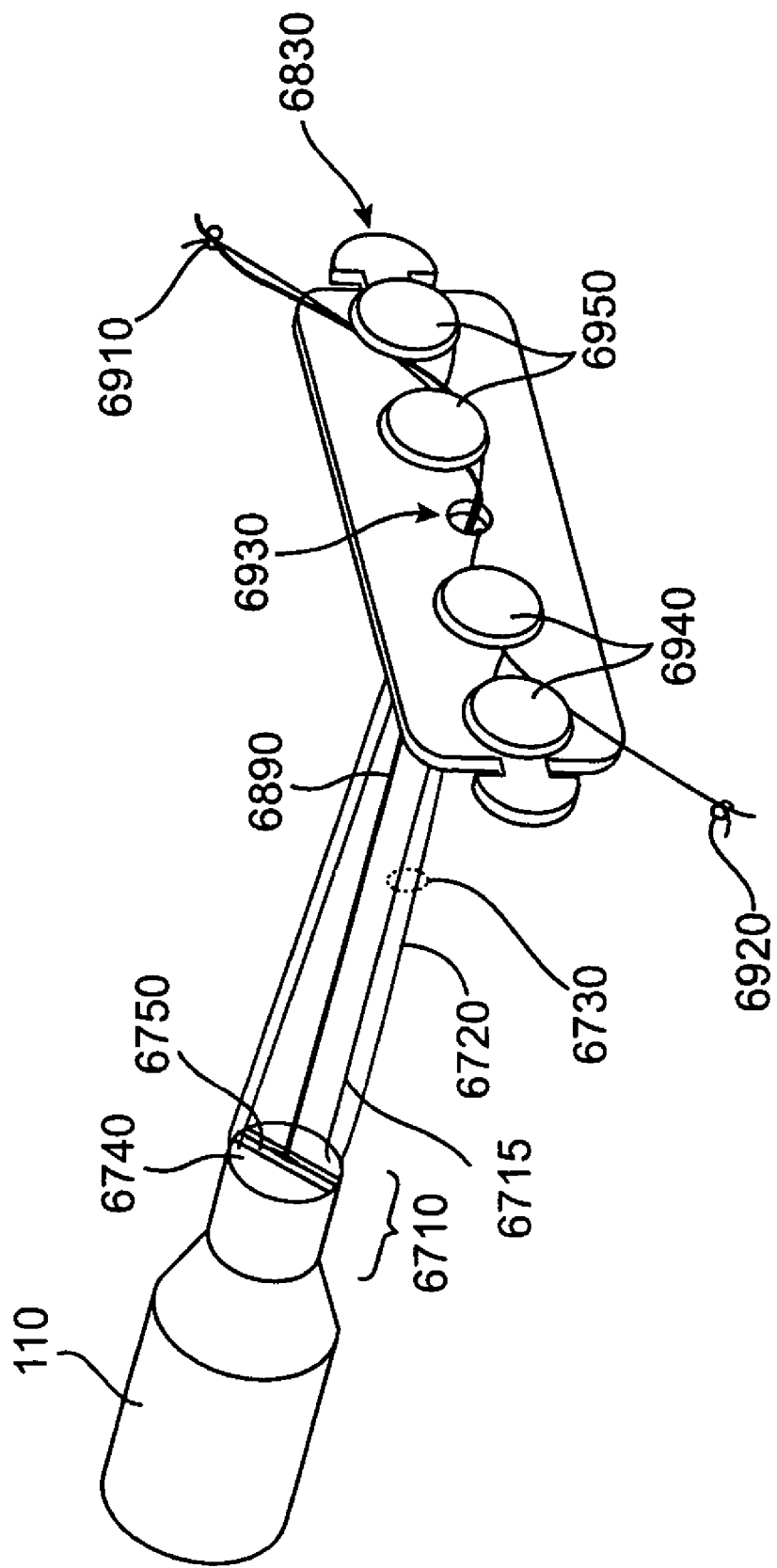

FIG. 29 shows an exploded view of the suture puller assembly 6820 of the loader assembly 6500. The suture puller assembly 6820 is configured to attach to the loops 6730, which are attached to the flow control device 110 as describe above with reference to FIG. 28. With the suture puller assembly 6820 attached to the flow control device 110 via the suture loops 6730, the suture puller assembly can be used to pull the flow control device 110 through the loading region 3622 and into the transfer region 3641 and/or housing region 3630 of the funnel housing 6620 pursuant to loading of the flow control device 110 into a container, such as the catheter housing 2940.

With reference to FIG. 29, the suture puller assembly 6810 includes a suture puller housing 6820, a suture attachment bar 6830, a number of suture loops 6730, a suture puller end cap 6840, and one or more end cap attachment screws 6630 that attach the end cap 6840 to one end of the suture puller housing 6820. The suture puller housing 6820 is a tubular housing that is configured to mate with the funnel housing 6620. In an exemplary embodiment, the suture puller housing 6820 is sized to receive the funnel housing 6620 therein in a sliding fashion.

The suture puller housing 6820 has a flange on a first end that attaches to the end cap 6840 with the suture attachment bar 6830 positioned therebetween. The sutures 6730 extend from the flow control device 110 through the housing 6820 and attach to the suture attachment bar 6830, as described below. It should be appreciated that the shape of the housing 6820 is not limited to a cylindrical shape as shown in FIG. 29, but can be other shapes.

FIG. 30 shows how the suture loops 6730 attach to the suture attachment bar 6830. In actual use, the suture attachment bar 6830 is attached to the suture puller housing 6820, which mates with the funnel housing 6620. For clarity of illustration, however, the suture puller housing 6820 and funnel housing 6620 are not shown in FIG. 30. The suture attachment bar 6830 includes outside strand retainers 6940 and inside strand retainers 6950, which are structures that are sized and shaped for attachment to the suture loops, such as by winding a portion of the loops around the retainers.

With reference still to FIG. 30, all five of the inside strands 6715 are tied together to form an inside suture knot 6910 and all five of the outside strands 6720 are also tied together to form an outside suture knot 6920. To fix the suture loops 6730 to the suture puller assembly 6810, the outside suture knot 6920 and the inside suture knot 6910 are passed through the center of the suture puller housing 6820 and through a suture hole 6930 that passes through the center of the suture attachment bar 6830. The suture attachment bar 6830 is mounted to the suture puller housing 6820 (such as shown in FIG. 29), and the inside strands 6715 are wound a number of times around the inside strand retainers 6950 to fix them in place. Likewise, the outside strands 6720 are wound a number of times around the outside strand retainers 6940 to fix them in place.

FIG. 29 shows the flow control device 110 attached to the sutures with the sutures extending through the suture puller housing 6820 and attached to the suture attachment bar 6830. The suture puller end cap 6840 is then attached with one or more end cap attachment screws 6630 to the suture puller housing 6820 to fix the suture attachment bar 6830, the inside strands 6715 and the outside strands 6720 in place. Of course, the suture strands could be fixed to the suture puller assembly 6810 in many different other ways including by using glue, screws, etc.

In use, the sutured flow control device 110 is positioned in the funnel-shaped loading region 3622 of the funnel housing 6620 and the end cap 6640 is attached to the funnel housing 6620 to secure the flow control device 110 therein. The sutures are positioned so that they extend through the transfer region 3641 and the housing region 3630. The sutures are then attached to the suture puller assembly 6820 via the suture attachment bar 6830 as described above. The suture puller assembly 6820 is coupled to the funnel assembly 6610 such that the assembled loader assembly 6500 is as shown in FIG. 26. As mentioned, the suture puller housing 6820 receives funnel housing 6620 to couple the suture puller assembly and funnel assembly together.

At this stage, the flow control device is positioned at one end of the loader assembly 6500 (within the loading region 3622) with the sutures attached to both the flow control device 110 and to the suture attachment bar 6830, which is positioned on the other end of the loader assembly 6500. When the suture puller assembly 6810 is pulled in the direction 4415 relative to the funnel assembly 6610 as shown in FIG. 26, the sutures pull the flow control device 110 through the loading region 3622, thus compressing the diameter of the flow control device 110, until it is completely compressed into the compressed state in the transfer region 3641.

At this stage, the suture loops 6730 can be cut manually on one side of each loop, either on an inside strand 6715 or on an outside strand 6720, and the suture pulled free of the compressed flow control device 110. As in the previous embodiment, once the suture loops 6730 are removed, the catheter 2915 and catheter housing 2940 can be connected to the funnel assembly 6610 by opening the locking mechanism 3640 and inserting the distal end of the catheter housing 2940 into the housing region 3630 of the funnel housing 6620. The locking mechanism is then closed to fix the catheter housing 2940 relative to the funnel assembly 6610, and the compressed flow control device 110 may then be transferred into the catheter housing 2940 by pushing it through the transfer region 3641 and into the catheter housing, such as by using the pusher 3520.

Figure 31:
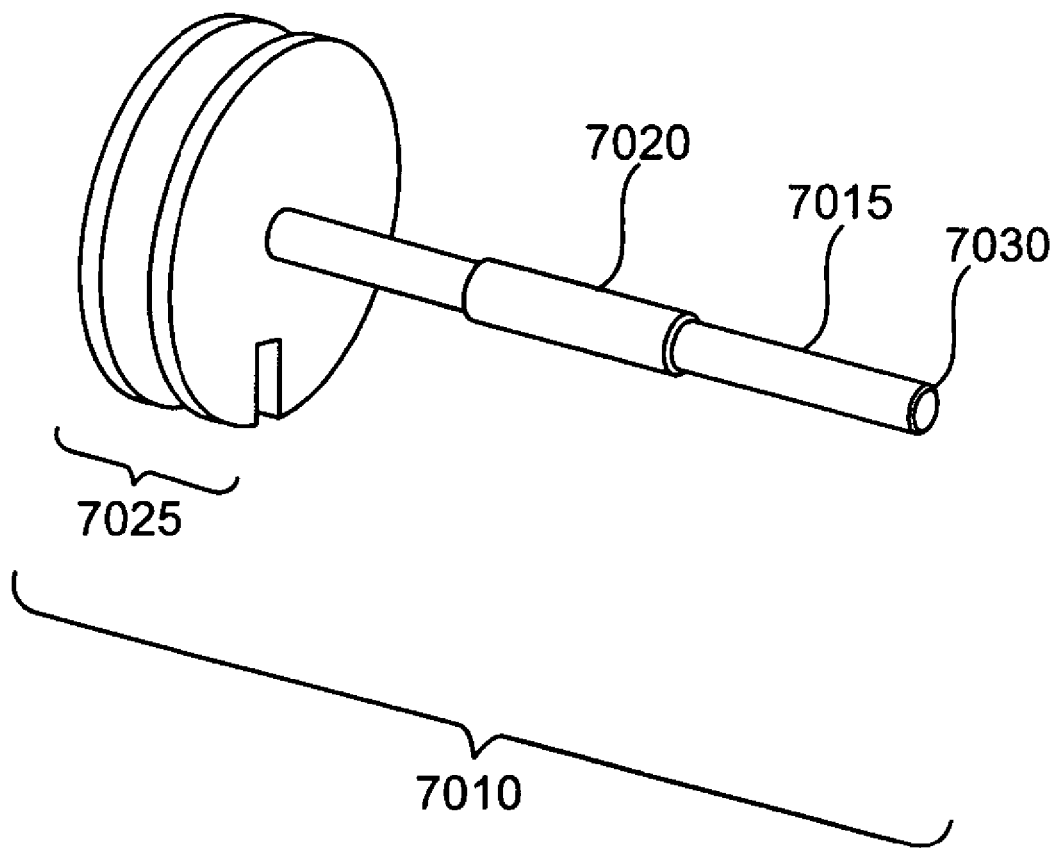
FIG. 31 shows a suture cutter assembly configured for use with the loader system for automatically cutting the suture loops.

In an alternative embodiment, the loader assembly 6500 is configured to automatically disengage the pulling structure 4410 from the flow control device. For example, the loader assembly 6500 can automatically cut the suture loops when the suture puller assembly 6810 and the funnel assembly 6610 are pulled apart, thus eliminating the need for the operator to manually cut the suture loops 6730. FIG. 31 shows a suture cutter assembly 7010, which is configured for use with the loader assembly 6500 for automatically cutting the suture loops. The suture cutter assembly 7010 is comprised of a cutting tube 7015, a suture cutter lock 7020, and a suture cutter guide 7025. The cutting tube 7015 can be a stainless steel tube with a sharpened cutting edge 7030, however it could be made of many other materials such as steel, brass, etc. that can be formed with a sharpened tip.

The suture cutter lock 7020 is cylindrical tube with an outer diameter that is greater than the outer diameter of the cutting tube 7015. The suture cutter lock 7020 has an outer dimension that is sized to slidably fit within the housing region 3630 of the funnel housing 6620. The suture cutter lock 7020 is formed over or otherwise attached to the outside of the cutting tube 7015.

The suture cutter guide 7025 has an outside dimension that is sized to slidably fit through the inner diameter of the suture puller housing 6820, and is attached to the cutting tube 7015 at an end opposite the sharpened end. All three portions of the suture cutter assembly 7010 can be formed of one piece, or may be formed of two or more separate components or materials and are bonded or otherwise attached to each other to form the suture cutter assembly 7010.

The suture cutter assembly 7010 is connected to the funnel assembly 6610 by opening the door 3645 of the locking mechanism 3640 and inserting the cutting tube 7015 through the door 3645 and into the housing region 3630. The suture cutter assembly 7010 is thereby connected to the funnel assembly 6610 as shown in FIG. 32. When the door 3645 is released and allowed to move into the locked position, the suture cutter lock 7020 is captured behind the door 3645 thus locking the suture cutter assembly 7010 to the funnel assembly 6610.

When the loader assembly 6500 is assembled, the suture loops that are threaded through the proximal end 6710 of the flow control device 110 are threaded through the center of the cutting tube 7015 portion of the suture cutter assembly 7010 before being attached to the suture attachment bar 6830 of the suture puller assembly 6810. When device loading is initiated, the suture puller assembly 6810 is pulled in the direction 4415 (FIG. 26) relative to the funnel assembly 6610, and the suture loops 6730 are pulled through the cutting tube 7015 and the flow control device 110 is drawn through the loading region 3622, thus compressing the diameter of the flow control device 110.

When the flow control device is almost completely drawn into the compressed state in the transfer region 3641, the outside strands 6720 of the suture loops 6730 are drawn against the cutting edge 7030 of the cutting tube 7015, and are severed. As the user continues to move the suture puller assembly 6810 in the direction 4415, the inside strands 6715 of the suture loops 6730 are pulled free of the now compressed flow control device 110. As the user continues to move the suture puller assembly 6810 in the direction 4415, a door release rib 6850 (shown in FIG. 29) mounted to the inner surface of the suture puller housing 6820 contacts the edge of the locking mechanism door 3645 causing it to rotate and open, thus disengaging from the suture cutter lock 7020.

As the suture puller assembly continues to move in the direction 4415, the edge of the suture cutter guide 7025 contacts the door release rib 6850 and the suture cutter assembly 7010 is drawn out of the funnel assembly 6610 and is retained inside the suture puller housing 6820 (and thus is retained with the suture puller assembly 6810). Now the funnel assembly contains the compressed flow control device 110 in the transfer region 3641, and the suture loops 6730 and the suture cutter assembly 7010 are entirely contained in the suture puller assembly 6810.

As in the previous embodiment, the catheter 2915 and catheter housing 2940 can now be connected to the funnel assembly 6610 by opening the locking mechanism 3640 and inserting the distal end of the catheter housing 2940 into the housing region 3630 of the funnel housing 6620. The locking mechanism is then closed to fix the catheter housing 2940 relative to the funnel assembly 6610, and the compressed flow control device 110 may then be transferred into the catheter housing 2940 by pushing it through the transfer region 3641 and into the catheter housing, such as by using the pusher 3520.

In the previous described embodiments, the flow control device is contained in the loader assembly 6500, and the delivery catheter 2915 is a separate device. In this way, the user may load and deliver multiple flow control devices 110 with the same delivery catheter 2915. However this requires the user to perform the multiple steps of actuating the loader assembly 6500 to compress the flow control device 110 into the transfer region 3641 of the funnel housing 6620, then loading the catheter housing 2940 into the funnel and transferring the compressed flow control device into the housing using the pusher 3520.

In an alternate embodiment, the catheter has an open center lumen and the catheter housing 2940 is preloaded into the housing region 3630 of the funnel housing 6620 when the device is presented to the user. The suture cutter assembly 7010 is eliminated from the funnel assembly 6610, and the suture loops 6730 are threaded through the catheter housing 2940 and through the inner lumen of the delivery catheter. The proximal ends of the suture loops 6730 can emerge from the catheter at point along its length that is proximal to the connection between the catheter housing 2940 and the shaft of the catheter.

To load the flow control device 110, the proximal ends of the suture loops 6730 are pulled and the flow control device is drawn through the loading region 3622 and directly into the catheter housing 2940. It would not be necessary to have a transfer region 3641 in the funnel housing 6620 as shown in the embodiment illustrated in FIG. 25A as the flow control device is pulled directly into the catheter housing 2940. Either the inside strands 6715 or the outside strands 6720 are then severed, either automatically by a cutting mechanism or manually by the user, the inside strands 6715 and the outside strands 6720 are withdrawn from the funnel assembly 6610, and the funnel removed from the catheter housing 2940. The flow control device 110 is now ready for delivery into the patient.

Valve Dilation

If the flow control device 110 comprises a valve 6740 (FIG. 28), either one-way or two-way, it is important that the lips of the valve 6740 not be stuck together when the device is implanted into a human bronchial lumen as the function of the valve 6740 may be impaired. This can occur following sterilization as the elevated temperatures and sterilant gas or fluid used in some sterilization techniques, such as ethylene oxide sterilization, can cause the lips of the valve 6740 to become stuck together. This is especially likely if the valve 6740 is manufactured from silicone, a material that is susceptible to sticking to itself. To insure that the valve lips 6750 are not stuck together after loading into the delivery catheter, the valve lip 6750 surfaces that contact each other can be coated with any of a number of different coatings that improve lubricity of silicone and discourage sticking. Possible valve lip 6750 coatings include parylene, various synthetic passivation coatings produced by SurModics, Inc. (Eden Prairie, Minn.), hydrophilic coatings such as hyaluronan, ion implanted silver or ceramic, etc. A similar effect can be achieved by impregnating the silicone with a lubricious substance such as PTFE prior to molding.

Another method for insuring that the valve lips 6750 are not stuck together after implantation is to physically dilate or open the valve lips 6750 prior to loading the flow control device into the catheter housing. One embodiment of a device for accomplishing this is shown in FIG. 29, where a dilator 6890 is placed through the lips of the valve 6740 of the flow control device 110 to insure that the lips are not stuck together. The dilator 6890 at least partially separates the lips from one another to prevent the lips from sticking together. The dilator 6890 is secured to the suture attachment bar 6830, the suture puller end cap 6840, the suture puller housing 6820 or any other portion of the suture puller assembly 6820. The dilator 6890 can be made of any material that, when placed through the valve lips 6750 of the flow control device 110, does not distort the shape of the valve 6740 such that the material would take a permanent set. The dilator 6890 can be a length of nylon, polypropylene or polyethylene suture, a flat ribbon of polyethylene, or any other flexible material or other shape.

The dilator thickness, or diameter in the case of a round cross-section material, is preferably between 0.001" and 0.008", however other dimensions are possible as long as it keeps the valve lips 6750 from sticking together. If the dilator is a flat ribbon of material, it can be as wide as the width of the valve opening, or can be narrower.

The dilator 6890 is threaded through the mouth of the valve 6740 of the flow control device 110, through the center of the cutting tube 7015 that is located inside the housing region of the funnel housing 6620, and is connected to the suture attachment bar 6830 along with the inside strands 6715 and the outside strands 6720. When device loading is initiated, the suture puller assembly 6810 is pulled in the direction 4415 relative to the funnel assembly 6610, the flow control device 110 is compressed into the transfer region, and the inside strands 6715 of the suture loops 6730 are severed by the cutting edge 7030 of the cutting tube 7015. The compressed flow control device 110 no longer moves when the suture puller assembly is pulled, however the dilator 6890 is not severed by the cutting edge 7030 and is thus pulled out of the valve lips 6750 of the flow control device 110 when the suture puller assembly is pulled free of the funnel assembly 6610. The compressed flow control device can be transferred into the catheter housing 2940 as described previously.

Alternately, the dilator 6890 can be removed from the loader in a first step, and then the loading sequence described previously can be performed in a second step. The dilator 6890 is pulled out of the loader assembly 6500 directly by the user, or it can be attached to a handle or other graspable object to aid in removal of the dilator 6890 prior to initiating the loading steps. In another embodiment, the dilation step may be performed before the flow control device 110 is compressed and loaded into the catheter housing 2940 by inserting a rigid dilation tool through the valve lips 6750 of the flow control device 110. This dilation tool can be a loop of metal wire, a blunt tipped metal or plastic rod, or any other shape or material that can fit through the valve mouth without cutting or tearing the valve material.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. An assembly for loading a bronchial flow control device into a container, comprising:
   a funnel housing defining an internal, funnel-shaped loading cavity that gradually reduces in size moving in a first direction, the loading cavity sized to receive a bronchial flow control device in an expanded state;
   a puller housing removably attached to the funnel housing, wherein the puller housing is removably attachable to a bronchial flow control device that can be positioned in the loading cavity, wherein the puller housing pulls the bronchial flow control device in the first direction through the funnel housing to gradually contract the bronchial flow control device into a compressed state of reduced size relative to the expanded state; and
   a pushing member configured to push the bronchial flow control device out of the funnel housing after the bronchial flow control device has been pulled through the loading cavity to be contracted into the compressed state.

2. An assembly as in claim 1, further comprising a suture attached to the puller housing for removably attaching the puller housing to the bronchial flow control device positioned in the loading cavity.

3. An assembly as in claim 2, further comprising a cutting mechanism that automatically cuts the suture when the puller housing has pulled the bronchial flow control device into the compressed state.

4. An assembly as in claim 1, wherein the funnel housing further defines an internal transfer cavity that communicates with the loading cavity, the transfer cavity sized to receive the bronchial flow control device from the loading cavity and retain the bronchial flow control device in the compressed state.

5. An assembly as in claim 4, wherein the funnel housing further defines a container cavity that communicates with the transfer cavity, the container cavity sized to receive a container that receives the bronchial flow control device in the compressed state.

6. An assembly for loading a bronchial flow control device into a container, comprising:
- a funnel housing defining an internal, funnel-shaped loading cavity that gradually reduces in size moving in a first direction, the loading cavity sized to receive a bronchial flow control device in an expanded state;
- a bronchial flow control device positioned in the loading cavity, the bronchial flow control device configured for placement in a bronchial passageway to regulate fluid flow through the bronchial passageway, and configured to form a seal with an interior wall of the bronchial passageway;
- a puller housing removably attached to the funnel housing;
- a pulling structure removably attaching the puller housing to the bronchial flow control device, wherein the puller housing and the pulling structure pull the bronchial flow control device in the first direction through the funnel housing to gradually contract the bronchial flow control device into a compressed state of reduced size relative to the expanded state; and
- a detachment mechanism that automatically detaches the pulling structure from the bronchial flow control device after the bronchial flow control device has been pulled and contracted into the compressed state.

7. An assembly as in claim 6, wherein the pulling structure comprises at least one suture.

8. An assembly as in claim 6, wherein the bronchial flow control device includes a valve with a pair of lips that open and close relative to one another, and wherein the assembly further comprises a dilator positioned between the lips of the valve to prevent the lips from sticking to one another.

9. An assembly as in claim 6, wherein the funnel housing further defines an internal transfer cavity that communicates with the loading cavity, the transfer cavity sized to receive the bronchial flow control device from the loading cavity and retain the bronchial flow control device in the compressed state.

10. An assembly as in claim 6, wherein the puller housing and the funnel housing slidably attach to one another.

11. A bronchial flow control device assembly, comprising:
- a funnel housing having an internal loading cavity and an internal transfer cavity, the loading cavity being funnel-shaped and having an outer dimension that gradually reduces from a large size to a small size, the transfer cavity communicating with a first end of the loading cavity and having an outer dimension that is substantially equal to the small size of the loading cavity;
- a bronchial flow control device positioned in the loading cavity while in an expanded state, the bronchial flow control device configured for placement in a bronchial passageway to regulate fluid flow through the bronchial passageway; and
- a puller housing removably connected to the funnel housing in a sliding fashion, the puller housing having a puller structure that connects the puller housing to at least a portion of the bronchial flow control device, wherein the puller housing slidably disconnects from the funnel housing such that the puller structure pulls the bronchial flow control device through the loading cavity and into the transfer cavity such that the bronchial flow control device is contracted into a compressed state when positioned in the transfer cavity wherein the puller housing and the funnel housing slidably are slidably attached to one another.

12. An assembly as in claim 11, wherein the pulling structure comprises at least one suture.

13. An assembly as in claim 11, further comprising a detachment mechanism that automatically detaches the pulling structure from the bronchial flow control device after the bronchial flow control device has been pulled into the compressed state.

14. An assembly as in claim 11, wherein the bronchial flow control device includes a valve with a pair of lips that open and close relative to one another, and wherein the assembly further comprises a dilator positioned between the lips of the valve to prevent the lips from sticking to one another.

* * * * *